Figure 2:
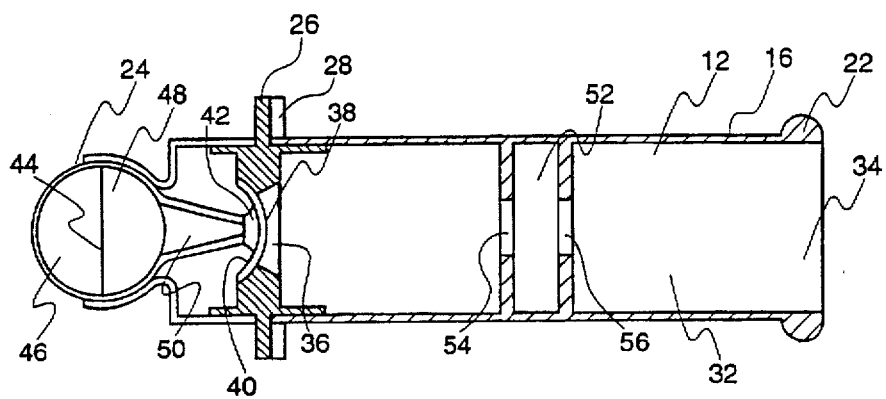

United States Patent [19]

Ivri et al.

[11] Patent Number: 5,758,637
[45] Date of Patent: *Jun. 2, 1998

[54] LIQUID DISPENSING APPARATUS AND METHODS

[75] Inventors: Yehuda Ivri, Irvine; Cheng H. Wu, Sunnyvale, both of Calif.

[73] Assignee: AeroGen, Inc., Sunnyvale, Calif.

[ * ] Notice: The term of this patent shall not extend beyond the expiration date of Pat. No. 5,586,550.

[21] Appl. No.: 604,313

[22] Filed: Feb. 21, 1996

Related U.S. Application Data

[63] Continuation-in-part of Ser. No. 521,641, Aug. 31, 1995, Pat. No. 5,586,550.

[51] Int. Cl.$^6$ ............................................. A61M 11/50
[52] U.S. Cl. ........................... 128/200.16; 128/200.14; 128/200.18; 239/102.2
[58] Field of Search ................... 128/200.16, 200.14, 128/200.18, 200.21; 239/102.2, 120, 406

[56] References Cited

U.S. PATENT DOCUMENTS

| | | | |
|---|---|---|---|
| 2,266,706 | 12/1941 | Fox et al. | 128/200.21 |
| 3,812,854 | 5/1974 | Michaels et al. | |
| 4,119,096 | 10/1978 | Drews | |
| 4,159,803 | 7/1979 | Cameto et al. | 239/102 |
| 4,268,460 | 5/1981 | Boiarski et al. | 128/200.21 |
| 4,300,546 | 11/1981 | Kruber | 128/200.16 |
| 4,301,093 | 11/1981 | Eck | 128/200.16 |
| 4,334,531 | 6/1982 | Reichl et al. | 128/200.14 |
| 4,338,576 | 7/1982 | Takahashi et al. | 331/67 |
| 4,454,877 | 6/1984 | Miller et al. | 128/200.21 |
| 4,465,234 | 8/1984 | Maehara et al. | 239/102 |
| 4,533,082 | 8/1985 | Maehara et al. | 239/102 |
| 4,632,311 | 12/1986 | Nakane et al. | 239/101 |
| 4,790,479 | 12/1988 | Matsumoto et al. | 239/102.2 |
| 4,793,339 | 12/1988 | Matsumoto et al. | 128/200.16 |
| 4,850,534 | 7/1989 | Takahashi et al. | 239/102.2 |
| 4,877,989 | 10/1989 | Drews et al. | 128/200.16 |
| 4,976,259 | 12/1990 | Higson et al. | 128/200.18 |
| 5,063,922 | 11/1991 | Häkkinen | 128/200.16 |

(List continued on next page.)

FOREIGN PATENT DOCUMENTS

| | | | |
|---|---|---|---|
| 0178925 | 4/1986 | European Pat. Off. | 128/200.16 |
| 477 885 | 10/1969 | Switzerland | |
| 2 101 500 | 1/1983 | United Kingdom | |
| 2101550 | 1/1983 | United Kingdom | 128/200.16 |
| 2 272 389 | 5/1994 | United Kingdom | |
| 2272389 | 5/1994 | United Kingdom | |

OTHER PUBLICATIONS

D.C. Cipolla et al., "Assessment of Aerosol Delivery Systems for Recombinant Human Deoxyribonuclease," *S.T.P. Pharma Sciences* 4 (1) 50–62, 1994.

D.C. Cipolla et al., "Characterization of Aerosols of Human Recombinant Deoxyribonuclease I (rhDNase) Generated by Jet Nebulizers," *Pharmaceutical Research* II (4) 491–498, 1994.

I. Gonda, "Therapeutic Aerosols," *Pharmaceutics, The Sci. of Dosage Form Design*, M.E. Aulton, 341–358, 1988.

Anthony J. Hickey, "Pharmaceutical Inhalation Aerosol Technology," *Drugs and The Pharmaceutical Sciences*, (54) 172–173.

*Primary Examiner*—Aaron J. Lewis
*Assistant Examiner*—V. Srivastava
*Attorney, Agent, or Firm*—Townsend and Townsend and Crew LLP

[57] ABSTRACT

The invention provides methods and apparatus for nebulizing liquids. In one exemplary embodiment, an apparatus is provided which comprises a thin shell member having a front surface, a rear surface, and a plurality of apertures extending therebetween. The apertures are tapered to narrow from the rear surface to the front surface. A liquid supplier is further provided which delivers a predetermined unit volume of liquid to the rear surface. A vibrator vibrates the thin shell member to eject liquid droplets from the front surface of the thin shell member.

22 Claims, 18 Drawing Sheets

U.S. PATENT DOCUMENTS

| | | | |
|---|---|---|---|
| 5,076,266 | 12/1991 | Babaev | 128/200.16 |
| 5,139,016 | 8/1992 | Waser | 128/200.16 |
| 5,152,456 | 10/1992 | Ross et al. | 239/102.2 |
| 5,164,740 | 11/1992 | Ivri | 346/1.1 |
| 5,170,782 | 12/1992 | Kocinski | 128/200.16 |
| 5,261,601 | 11/1993 | Ross et al. | 128/200.16 |
| 5,312,281 | 5/1994 | Takashashi et al. | 128/200.16 |
| 5,415,161 | 5/1995 | Ryder | 128/200.23 |
| 5,487,370 | 1/1996 | Robertson et al. | 128/200.16 |
| 5,487,378 | 1/1996 | Robertson et al. | 128/200.16 |
| 5,515,841 | 5/1996 | Robertson et al. | 128/200.21 |
| 5,518,179 | 5/1996 | Humberstone et al. | 239/102.2 |
| 5,533,497 | 7/1996 | Ryder | 128/200.21 |
| 5,579,575 | 12/1996 | McMahon et al. | 128/200.21 |
| 5,586,550 | 12/1996 | Ivri et al. | 128/200.16 |

LIQUID DISPENSING APPARATUS AND METHODS

CROSS REFERENCE TO RELATED APPLICATIONS

This application is a continuation-in-part application of U.S. application Ser. No. 08/521,641 now a U.S. Pat. No. 5,586,550, filed Aug. 31, 1995, the complete disclosure of which is herein incorporated by reference.

BACKGROUND OF THE INVENTION

1. Field of the Invention

This invention relates generally to the field of therapeutic drug delivery, and in particular to the delivery of therapeutic liquids to the respiratory system.

A wide variety of procedures have been proposed to deliver a drug to a patient. Of particular interest to the present invention are drug delivery procedures where the drug is in liquid form and is delivered to the patient's lungs. Effective intrapulmonary drug delivery depends on a variety of factors, some of which can be controlled by the clinician or scientist and others that are uncontrollable. Uncontrollable factors include, among others, the airway geometry of the patient's respiratory tract and lung and other respiratory diseases. Of the controllable factors, two are of particular interest. The first is the droplet size and droplet size distribution. The second is the breathing pattern.

A major factor governing the effectiveness of drug deposition in the lungs is the size of the inspired particles. Depending on the particle size, total deposition in various regions of the lung may vary from 11% to 98%. See Heyder et al., *Aerosol Sci.*, 1986, 17, 811–825, the disclosure of which is herein incorporated by reference. Therefore, proper selection of particle size provides a way to target liquid droplets to a desired lung region. It is particularly difficult, however, to generate a liquid spray in which all the droplets will have the same size or the same aerodynamic behavior such that drug deposition in the desirable lung region is predictable.

A parameter that may be used to define droplet size is the respirable fraction (RF). The respirable fraction (RF) is defined as the fraction of the mass of aerosol droplets falling between a particular size range, usually in the range from about 1 μm to 6 μm. See D. C. Cipolla, et al., *Assessment of Aerosol Delivery Systems for Recombinant Human Deoxyribonuclease*, S.T.P. Pharma Sciences 4(1) 50–62, 1994, the disclosure of which is herein incorporated by reference. As used hereinafter, the term respirable fraction (RF) will include the percentage of droplets having sizes falling in the range of from about 1 μm to 6 μm. Another parameter that may be used to evaluate nebulization performance is the efficiency (E). The efficiency (E) of a nebulizer is the amount of liquid which is actually aerosolized and leaves the nebulizer in aerosolized form as compared to the amount of liquid that is initially supplied to the nebulizer. See D. C. Cipolla, et al., *Assessment of Aerosol Delivery Systems for Recombinant Human Deoxyribonuclease*, S.T.P. Pharma Sciences 4(1) 50–62, 1994. Still another parameter that may be used to measure the performance of nebulizers is the delivery percentage (D) which is the respirable fraction (RF) multiplied by the efficiency (E). See D. C. Cipolla, et al., *Assessment of Aerosol Delivery Systems for Recombinant Human Deoxyribonuclease*, S.T.P. Pharma Sciences 4(1) 50–62, 1994.

A variety of inhalation devices have been proposed including air jet nebulizers, ultrasonic nebulizers, and metered dose inhalers (MDIs). Air jet nebulizers usually utilize a high pressure air compressor and a baffle system that separates the small particles from the spray. Ultrasonic nebulizers generate ultrasonic waves with an oscillating piezoelectric crystal to produce liquid droplets. Another type of ultrasonic nebulizer of interest is described in U.S. Pat. Nos. 5,261,601 and 4,533,082. This nebulizer includes a housing that defines a chamber for holding a quantity of liquid to be dispensed. A perforated membrane is held over the chamber and defines a front wall of the chamber, with the rear surface of the membrane being in constant contact with the reservoir of liquid held in the chamber. The apparatus further includes an ultrasonic vibrator connected to the housing to vibrate the perforated membrane. Typical MDIs usually employ a gas propellant, such as CFC, which carries the therapeutic substance and is sprayed into the mouth of the patient.

Most commercially available inhalers produce sprays having a respirable fraction (RF) of 80% or less, with ultrasonic nebulizers usually having a respirable fraction (RF) of less than about 50%, thereby making dosing control difficult and inaccurate. Presently, most commercially available inhalers also have a poor efficiency (E), usually less than about 60%. See D. C. Cipolla, et al., *Assessment of Aerosol Delivery Systems for Recombinant Human Deoxyribonuclease*, S.T.P. Pharma Sciences 4(1) 50–62, 1994. Such inefficiency often results from the construction of the nebulizer since a certain amount cannot be nebulized and remains within the device. Since most commercially available nebulizers have both a poor respirable fraction (RF) and a poor efficiency (E), the delivery percentage (D) is also poor. Therefore, such inhalers have generally not been used for delivery of drugs that have potent therapeutic agents such as hormones and peptides or other drugs having a high level of toxicity and which can be expensive.

The second factor influencing droplet deposition is the patient's breathing pattern. Inhalation flow rate affects the probability of particle impact, while tidal volume and lung volume affect particle residence time in each lung region. Therefore, effective droplet deposition should be adaptable to the inhalation flow rate as well as the patient's tidal volume and lung volume.

Other important factors often considered when designing an effective therapeutic drug delivery system include both cost and convenience. When nebulizing the medicament, the apparatus involved usually comes in contact with the medicament. Hence, the apparatus will need to be sterilized before reuse, or discarded. However, sterilization may not be convenient for a hand held portable device. Disposal can also be expensive, particularly when the apparatus includes a piezoelectric crystal for nebulizing the liquid.

It would therefore be desirable to provide improved apparatus and methods for the delivery of liquids to the respiratory system. Such apparatus and methods should be capable of producing a spray which may predictably be deposited in selected regions of the lungs. Further, it would be desirable if such a spray were produced from a small volume of liquid. Moreover, it would be desirable if the apparatus and methods provided for a controlled drug delivery rate, preferably being based on the rate of inspiratory air flow generated during inhalation. Finally, it would be desirable if such methods and devices were inexpensive, efficient, and easy to use.

2. Brief Description of the Background Art

U.S. Pat. No. 4,533,082 describes a vibrating orifice apparatus with a multiplicity of apertures for producing liquid droplets.

As previously described, U.S. Pat. No. 5,261,601 describes an atomizer having a membrane covering a liquid chamber.

Apparatus for atomizing liquids such as liquid fuel, water, liquid drugs are described in U.S. Pat. Nos. 3,812,854; 4,159,803; 4,300,546; 4,334,531; 4,465,234; 4,632,311; 4,338,576; and 4,850,534.

D. C. Cipolla, et al., *Assessment of Aerosol Delivery Systems for Recombinant Human Deoxyribonuclease*, S.T.P. Pharma Sciences 4(1) 50–62, 1994, previously incorporated by reference, describes various inhalation devices and provides selected data on their efficiency (E) and respirable fraction (RF) values.

Anthony J. Hickey, Ed., *Pharmaceutical Inhalation Aerosol Technology*, Drugs and the Pharmaceutical Sciences, Vol. 54, pages 172–173, describes a container and a metering valve for an MDI. The container is specifically designed to hold a propellant to produce a spray.

SUMMARY OF THE INVENTION

The present invention provides methods and apparatus for the delivery of therapeutic liquids to the respiratory system of a patient. In one exemplary embodiment, the apparatus of the present invention is characterized in that it is able to produce a spray having a respirable fraction (RF) of greater than about 70%, preferably more than about 80%, and most preferably more than about 90%. Preferably, the apparatus will eject the liquid at a flow rate of at least about 5 µl/sec, and preferably more than about 10 µl/sec. By producing such a spray, the aerodynamic behavior of all the droplets will be substantially the same, thereby enabling the apparatus to be useful in intrapulmonary drug delivery.

The apparatus will preferably include a vibratable non-planar surface or non-planar member with apertures extending therethrough. The non-planar member will preferably comprise a rigid thin shell member having a front surface, a rear surface, and a plurality of apertures extending therebetween. The apertures are tapered so that they narrow from the rear surface to the front surface. A liquid supplier is provided which delivers liquid to the rear surface such that substantially all of the delivered liquid adheres to the thin shell member, and particularly within the large opening of the tapered apertures, by surface tension, i.e. in surface tension contact. A vibrator is further provided which vibrates the thin shell member to eject liquid droplets from the front surface of the thin shell member. Preferably, the apertures will be configured to eject liquid droplets having a respirable fraction (RF) of greater than about 70%, preferably more than about 80%, and most preferably more than about 90%. In another preferable aspect, the apparatus will have an efficiency (E) at or closely approaching 100%, i.e. substantially all liquid supplied to the rear surface will be aerosolized and will be available for inhalation. In this way, the delivery percentage (D) will usually be about the same as the respirable fraction (RF), i.e. greater than about 70%.

In one exemplary aspect, the size of the apertures at the front surface is in the range from about 1 µm to 6 µm, with the apertures have a slope at the front surface of about 10° or greater relative to a central axis of the apertures, preferably being in the range from about 10° to 20° relative to the central axis of the apertures, and more preferably being in the range from about 10° to 15° relative to the central axis. Preferably, the thin shell member will have a thickness of about 50 µm to about 100 µm, more preferably from about 75 µm to about 100 µm which provides the thin shell member with sufficient rigidity to vibrate in unison and provides sufficient aperture volume. In the present invention, ejection of droplets is developed due to the solid/fluid interaction inside the aperture, i.e. the interaction of the liquid against the tapered wall of the aperture. The cross sectional geometry of the aperture is therefore important. For example, if the aperture has a straight cylindrical wall with a slope of 0° relative to the central axis (or a 90° slope relative to the front surface of the thin shell member), ejection will not occur. Instead, the vibratory motion will cause the liquid to break loose from the vibratory surface so that it will not eject through the aperture.

For apertures smaller than 6 µm, the slope near the exit opening of the aperture is particularly important because the discharge coefficient of such an aperture is substantially smaller than for larger apertures. For apertures smaller than 6 µm, a slight variation in the slope near the small opening of the aperture will make significant influence on ejection of droplets because the tapered shape near the opening increases the surface area that is subjected to solid/fluid interaction near the exit opening. For example, vibration of the thin shell member when the apertures have a slope of 20° (relative to the central axis of the apertures) near the small opening produces 10 times more droplets than when the apertures are at right angles to the front surface. In this manner, a high flow rate can be achieved using a small thin shell member. A small thin shell member is desirable in that it has higher structural rigidity which assists in producing a fine spray as described hereinafter.

In another exemplary aspect, the thin shell member is hemispherical, parabolic, arc shaped, or curved in geometry, with the large opening of each aperture being located at the concave side, and the small opening of each aperture being located at the convex side. The thin shell member is preferably formed to have a low mass and a very high stiffens which causes the thin shell member to oscillate as a rigid body, i.e. homogeneously. In this way, all the apertures in the thin shell member are subject to the same amplitude so that droplets may be produced with a uniform size and with a desired respiratory fraction.

In one particular embodiment, the invention provides an apparatus for nebulizing a liquid having a housing with a proximal end and a distal end. A non-planar member, and preferably a thin shell member, is mounted within the housing, with thin shell member having a plurality of apertures for nebulizing the liquid upon vibration of the thin shell member. A vibrator is provided and is removably attached about the housing which vibrates the thin shell member. Preferably, the thin shell member is mounted within a dynamically isolated portion of the housing. In this manner, the vibration is not transmitted to the housing allowing the vibrator to be dismantled and reinstalled over the housing as desired.

Advantageously, the elements that come in contact with the mouth of the patient or with of the therapeutic liquid are held within the housing. Prior to use, the housing is connected to the vibrator which transmits vibratory motion to the thin shell member inside the housing to produce ejection of droplets which are then entrained in the inspiratory air flow. In this manner, the vibrator will not come into contact with the liquid, thereby allowing the vibrator to be reused with a new and uncontaminated housing. Such a configuration provides an economical nebulizing apparatus since the relatively expensive vibrator may be reused.

In a further exemplary embodiment of the present invention, an apparatus is provided which ejects a liquid spray at a rate synchronized with the inspiratory flow created during inhalation so the that ejection rate is proportional to the inspiratory flow rate. The apparatus includes a housing having a distal end and a mouthpiece at a proximal end. A non-planar member, and preferably a thin shell member, is mounted within the housing, with the thin shell member having a plurality of apertures. A vibrator is provided to vibrate the thin shell member and to eject liquid from the apertures. An acoustic chamber is provided within the housing which produces an audible signal during inhalation from the mouthpiece. Further provided is a controller for controlling the rate of thin shell member vibration upon detection of the audible signal. Preferably, the controller includes a microphone which detects the audible signal so that an electrical signal may be sent to the vibrator.

In this manner, the patient may simply breath through the mouthpiece (or a nasal adapter) to control the rate of droplet production. The respiratory flow passes through the acoustic chamber which produces the acoustic tone which is proportional to the inspiratory flow rate. Thus, the frequency of the acoustic tone indicates the inspiratory flow rate at any instant of the breathing cycle. Integration of the flow rate with time produces the tidal volume. Both the flow rate and the tidal volume can then be used to determine when the ejector should eject droplets and at what mass flow rate such that maximum deposition of droplets is obtained. Further, the acoustic tone may be recorded to produce a record of the breathing pattern of the patient which may be stored in a microprocessor. This information can be later used to synchronize the ejection of droplets for the same patient. Such information may also be later employed for other diagnostic purposes.

The invention further provides a method for nebulizing a liquid. According to the method, a non-planar member, preferably a thin shell member, having a plurality of tapered apertures extending therethrough is vibrated. The apertures in the thin shell member are configured to produce liquid droplets having a respirable fraction (RF) of greater than about 70%, preferably more than about 80%, and most preferably more than about 90%. In a preferable aspect, liquid is supplied to the thin shell member such that substantially all of the delivered liquid adheres to the thin shell member by surface tension. In this manner, the need for a container or a chamber to hold the liquid against the thin shell member is eliminated. Instead, the liquid is open to the atmosphere and is not subjected to pressurization or reflecting acoustic waves that may be produced within an adjacent chamber. Preferably, liquid will be supplied to the thin shell member by squeezing a liquid reservoir which dispenses a discrete volume of liquid onto the thin shell member. Usually, substantially all liquid delivered to the thin shell member will be transformed into liquid droplets that are available for inhalation, i.e. the efficiency (E) will be at or near 100%. In this way, the delivery percentage (D) will be substantially the same as the respirable fraction (RF).

In another aspect, the method provides for producing the liquid droplets at a rate greater than about 5 μliters per second. In another aspect, the vibrating step further comprises vibrating substantially all of the apertures in the thin shell member in unison. Preferably, the thin shell member will be vibrated at a frequency in the range from about 45 kHz to 200 kHz. In yet another aspect, the thin shell member is held within a housing having a mouthpiece, and the thin shell member is vibrated at a rate corresponding to an inspiratory flow rate through the mouthpiece. In one preferable aspect, the thin shell member is vibrated only during inhalation from the mouthpiece. Control of shell member vibration in this manner may be accomplished by producing an audible signal during inhalation and detecting the produced signal.

In one particular aspect, the vibrating step comprises removably attaching a vibrating source about a housing enclosing the thin shell member and actuating the vibrating source. Optionally, the vibrating source may be removed from the housing and the housing discarded after use.

The invention provides a further exemplary method for delivering a liquid to the lungs of a patient. According to the method, a housing is provided having a proximal end and a distal end. Liquid is supplied to an thin shell member disposed within the housing, with the thin shell member having a plurality of tapered apertures extending therethrough. The patient then inhales from the proximal end of the housing at a selected inspiratory flow rate, and the thin shell member is vibrated to eject the liquid at a rate corresponding to the inspiratory flow rate.

In one aspect of the method, the inspiratory flow rate is variable. In another aspect, the vibrating step further comprises ejecting the liquid only during inhalation. In still a further aspect, an audible signal is produced during inhalation and the produced signal is detected to control the rate of vibration of the thin shell member.

The thin shell member will preferably be vibrated to produce liquid droplets having a respirable fraction (RF) of greater than about 70%, preferably more than about 80%, and most preferably more than about 90%. In another preferable aspect, liquid will be supplied to the thin shell member such that substantially all of the delivered liquid adheres to the thin shell member by surface tension. Preferably, substantially all of the apertures in the thin shell member will be vibrated in unison.

The invention further provides an exemplary apparatus for nebulizing a liquid. The apparatus is particularly useful in accurately dispensing discrete quantities of a liquid, such as a single unit dosage of a liquid medicament. The apparatus comprises a thin shell member comprising a front surface, a rear surface, and a plurality of apertures extending therebetween. The apertures are tapered to narrow from the rear surface to the front surface. A liquid supplier is provided to deliver a predetermined unit volume of liquid to the rear surface. A vibrator vibrates the thin shell member to eject liquid droplets from the front surface of the thin shell member. Hence, by delivering only a unit volume of liquid to the rear surface and ejecting the entire unit volume, an apparatus for precisely nebulizing a known unit volume of liquid is provided.

In one exemplary aspect, the liquid supplier comprises a canister which holds the liquid under pressure. Usually, the canister will comprise a storage reservoir and a valve which allows the predetermined unit volume of liquid to be delivered from the canister when the valve is in an open position. In a preferable aspect, the valve comprises a chamber having a piston therein and a stem having a proximal end and a distal end. The stem includes an elongate groove at the distal end which places the storage reservoir and the chamber in fluid communication when the valve is in a closed position so that the chamber may be filled with liquid from the storage reservoir. The stem further includes a lumen at the proximal end which is placed in fluid communication with the chamber when the valve is in the open position such that a unit volume of the liquid within the chamber is forced out of the lumen and onto the rear surface of the thin shell member upon translation of the piston.

In another particular aspect, a spring is included adjacent the piston so that the piston may be automatically translated to force the unit volume of liquid from the chamber when the valve is in the open position. The pressure within the storage reservoir then compresses the spring to allow the chamber to be refilled with liquid from the storage reservoir when the valve is in the closed position.

In still another aspect, an acoustical sensor is provided which detects when the unit volume of liquid has been ejected from the thin shell member. Preferably, the acoustical sensor comprises a piezoelectric element. In this manner, a user may be informed as to whether all of the liquid supplied to the thin shell member has been nebulized. In yet another aspect, the apparatus includes a mouthpiece and a means for actuating the vibrator when a patient begins to inhale from the mouthpiece.

The invention also provides an exemplary method for nebulizing a single unit volume of liquid, such as a unit dosage of a liquid medicament. According to the method, a thin shell member is provided which comprises a front surface, a rear surface, and a plurality of apertures extending therebetween. The apertures are tapered to narrow from the rear surface to the front surface. A valve is then opened to deliver a unit volume of the liquid from a container and to the rear surface of the thin shell member. The thin shell member is vibrated until substantially all of the unit volume of the liquid on the rear surface is ejected from the front surface.

In one particular aspect, a piston is translated within the container sufficient to expel the unit volume of the liquid from the container and onto the rear surface when the valve is opened. Preferably, the valve is spring biased so that the piston will automatically translate upon opening of the valve. In another aspect, the container holds the liquid under pressure so that the piston will be translated in an opposite direction by force of the liquid to compress the spring when the valve is closed. In this way, the container will be refilled when the valve is closed.

In one exemplary embodiment, the container comprises a canister which holds the liquid in a pressurized storage reservoir. The valve comprises a chamber having a spring loaded piston therein and a stem having a proximal end and a distal end and an elongate groove at the distal end which places the storage reservoir and the chamber in fluid communication when the valve is in a closed position. In this manner, opening of the valve is accomplished by depressing the valve stem to place a lumen at the proximal end of the stem in fluid communication with the chamber so that a unit volume of the liquid within the chamber will be forced out the lumen upon translation of the piston.

In another particular aspect, a step is provided for sensing when the unit volume of liquid has been ejected from the thin shell member. Preferably, such sensing is accomplished by detecting a change of an acoustical signal generated by the vibrating thin shell member to indicate when the unit volume has been ejected. Preferably, the acoustical signal is sensed with a piezoelectric element.

In yet another aspect, a mouthpiece is provided which is spaced-apart from the thin shell member. With such a configuration, a step is provided for sensing when a patient inhales from the mouthpiece and vibrating the thin shell member only during inhalation. In still another aspect, the unit volume of liquid that is nebulized is in the range from about 20 μl to about 100 μl.

The invention still further provides another exemplary apparatus for nebulizing a liquid. The apparatus comprises a thin shell member comprising a front surface, a rear surface, and a plurality of apertures extending therebetween, with apertures being tapered to narrow from the rear surface to the front surface. A liquid reservoir is provided, and a capillary system is in fluid communication with the liquid reservoir. The capillary system is disposed to draw liquid from the reservoir by capillary action for delivery to the rear surface of the thin shell member. A vibrator is also provided and vibrates the thin shell member to eject liquid droplets from the front surface of the thin shell member.

In one preferable aspect, the capillary system comprises a wicking member having a bottom end within the liquid reservoir and a delivery end near the rear surface of the thin shell member. An outer member is spaced-apart from the wicking member by a capillary gap so that liquid from the reservoir may be drawn through the capillary gap and toward the delivery end by capillary action. Preferably, the wicking member further includes at least one capillary channel at the delivery end so that liquid delivered from the capillary gap may continue its travel to the rear surface of the thin shell member through the capillary channel. In another preferable aspect, a bottom portion of the wicking member is cylindrical in geometry, and the outer member includes an annular body which surrounds the wicking member.

In one exemplary aspect, the apparatus further includes a housing having a chamber and a mouthpiece, with the outer member being attached to the housing. The wicking member is attached to the liquid reservoir which in turn is detachably secured to the housing so that the liquid reservoir may be separated from the housing. In another aspect, the wicking member includes a flexible portion so that it may axially flex upon contact with the vibrating member. In this way, contact of the wicking member will not interfere with the performance of the vibratable member.

In still yet another aspect, the liquid reservoir has a concave shape and includes capillary channels which move the liquid toward the capillary gap between the outer member and the wicking member. A power supply is further provided which supplies power to the vibrator. The power supply may comprise a battery, a rechargeable battery, an AC or a DC power source, or the like.

The invention still further provides an exemplary method for nebulizing a liquid by providing a thin shell member comprising a front surface, a rear surface, and a plurality of apertures extending therebetween. The apertures are tapered to narrow from the rear surface to the front surface. Liquid is drawn from a liquid reservoir by capillary action to place the liquid in contact with the rear surface of the thin shell member. The thin shell member is vibrated to eject the liquid on the rear surface from the front surface, with liquid being continuously supplied from the liquid reservoir to the rear surface as the thin shell member is vibrated. In this manner, substantially all of the liquid within the reservoir may be nebulized.

In one exemplary aspect, the capillary action is provided by a capillary gap between a wicking member and an outer member, with the wicking member having a bottom end within the liquid reservoir and a delivery end near the rear surface of the thin shell member. The capillary action may optionally be augmented by providing at least one capillary channel at the delivery end of the wicking member so that liquid from the capillary gap may continue its travel to the thin shell member.

Figure 1:
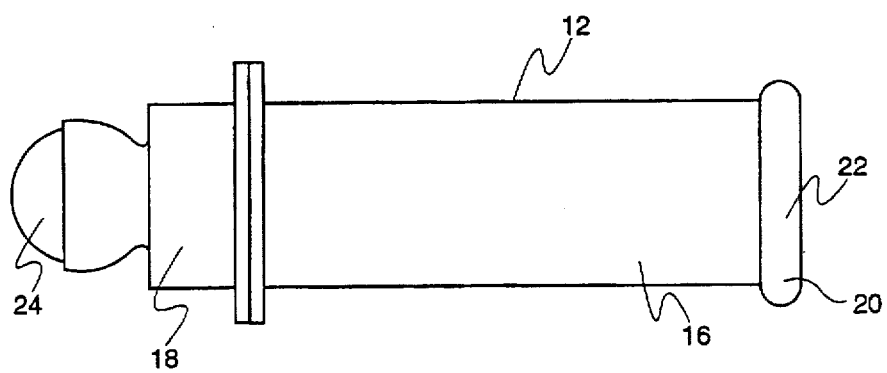
Figure 3:
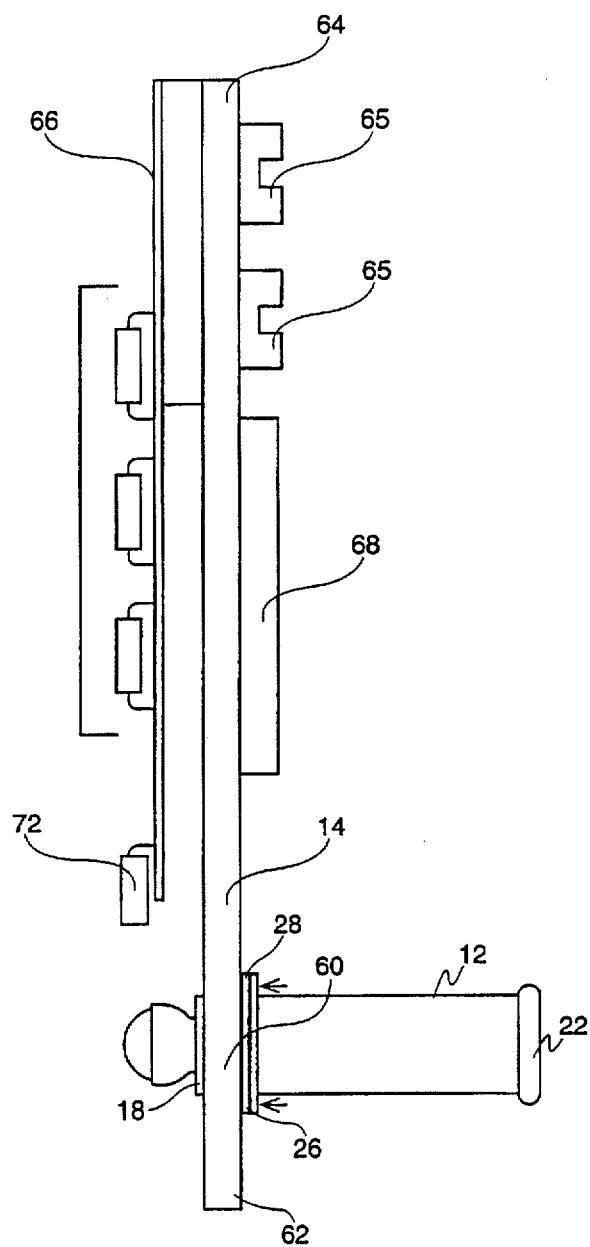

In another aspect of the method, a housing is provided having a chamber, a mouthpiece, the outer member, and the vibratable member. In this manner, the reservoir may be attached to the housing prior to vibrating the vibratable member. After nebulizing the liquid, the housing may be detached from the reservoir so that the housing and reservoir may be washed. In another exemplary aspect, the housing may be titled while nebulizing the liquid, thereby allowing a patient to inhale from the mouthpiece while lying down. In still another aspect, at least some of the liquid is transferred from the liquid reservoir and to the capillary gap by capillary action.

BRIEF DESCRIPTION OF THE DRAWINGS

FIG. 1 is a top view of a disposable mouthpiece assembly of a nebulizing apparatus according to the present invention.

FIG. 2 is a cross-sectional view of the mouthpiece assembly of FIG. 1.

FIG. 3 is a side view of an exemplary nebulizing apparatus having an oscillator assembly attached about the mouthpiece assembly of FIG. 1 according to the present invention.

FIG. 4 is a bottom view of a vibratory cantilever beam of the oscillator assembly of FIG. 3.

FIG. 5 illustrates a side view of the cantilever beam of FIG. 4, with the mode of vibration being shown in phantom line.

FIG. 6 is a cross-sectional side view of an exemplary aperture in a thin shell member according to the present invention.

FIG. 7 is a cross-sectional side view of an alternative aperture in a thin shell member according to the present invention.

FIG. 8 is a graph illustrating the relationship between the acoustic frequency produced by an acoustic chamber within the mouthpiece assembly of FIG. 1 and the inspiratory flow rate through the mouthpiece assembly according to the present invention.

FIG. 9 is a schematic view of a system for supplying a predetermined unit volume of liquid to a rear surface of a vibratable member according to the present invention.

FIG. 10 illustrates the system of FIG. 9 shown with a piston being translated to deliver the predetermined unit volume of liquid to the rear surface according to the present invention.

FIG. 11 is a perspective view of an exemplary apparatus for nebulizing a predetermined unit volume of liquid according to the present invention.

FIG. 12 is a perspective view of the apparatus of FIG. 11 illustrating an AC flip blade which may be inserted into an AC outlet according to the present invention.

FIG. 13 is a cross-sectional side view of the apparatus of the FIG. 11.

FIG. 13A is a side view of a thin shell member of the apparatus of FIG. 13.

FIG. 14 is an exploded view of a canister and a valve of the apparatus of FIG. 13.

FIG. 15 is a cross-sectional side view of the canister and valve of FIG. 14 with the valve shown in a closed position.

FIG. 16 illustrates the canister and valve of FIG. 15 in an open position.

FIG. 17 is an exploded perspective view of an alternative apparatus for nebulizing a liquid according to the present invention.

FIG. 18 is a perspective view of a wicking member of the apparatus of FIG. 17.

FIG. 19 is a cross-sectional side view of the apparatus of FIG. 17.

FIG. 20 is a more detailed view of a capillary system of the apparatus of FIG. 19.

FIG. 21 illustrates the apparatus of FIG. 19 with the wicking system being detached from the apparatus housing.

FIG. 22 illustrates the apparatus of FIG. 19 with a DC car adapter.

FIG. 23 is a side view of an AC plug that may be used with the apparatus of FIG. 19.

DETAILED DESCRIPTION OF THE SPECIFIC EMBODIMENTS

The invention provides methods and apparatus for producing a very fine spray useful in pulmonary drug delivery procedures. The invention provides for producing a spray having a respirable fraction (RF) of greater than about 70%, preferably more than about 80%, and most preferably more than about 90%. The efficiency (E) of the nebulization apparatus will usually be at or near 100%, leading to a delivery percentage (D) which is substantially the same as the respirable fraction (RF). Such a spray will preferably be produced at a flow rate of at least about 5 μl per second, and more preferably at least about 10 μl per second. In this manner, a spray of a selected size is produced where the aerodynamic behavior of all the droplets is substantially the same, thereby enabling the spray to be predictably deposited in selected regions of the lungs during intrapulmonary drug delivery procedures.

The invention may be employed to deliver a wide variety of drugs to the respiratory system, and will preferably be used to deliver drugs having potent therapeutic agents, such as hormones, peptides, and other drugs requiring precise dosing. Liquid drugs which may be nebulized using the present invention include drugs in solution form (e.g., in aqueous solution, ethanol solution, aqueous/ethanol mixture solution, and the like), in colloidal suspension form, and the like.

The invention will preferably be configured to supply the spray upon demand, i.e., the spray will be produced and delivered only upon inhalation by the patient. Further, such a spray will preferably be produced and delivered at a rate corresponding to the inhalation or inspiratory flow rate produced by the patient when inhaling the spray. In this manner, the spray will be produced only when the patient is inhaling, and will preferably be produced at a rate corresponding to the inhalation rate.

The invention will provide such a spray by providing the liquid to a vibratable non-planar member, which is preferably a thin shell member having a plurality of apertures. Liquid is preferably supplied to the thin shell member such that substantially all of the delivered liquid will adhere to the thin shell member by surface tension. Upon vibration of the thin shell member, the adhering liquid will be ejected through the apertures to form the fine spray. In this manner, a precise and controlled amount of liquid drug can be supplied to the thin shell member for nebulization, thereby eliminating the need for a fluid reservoir to be placed against the thin shell member.

Apertures in the thin shell member of the invention will preferably be tapered in geometry, with the smaller end of the aperture being located at a front surface of the thin shell member and the larger opening of the aperture being at the rear surface of the thin shell member. The size of the apertures at the front surface will preferably be in the range from about 1 μm to 6 μm, with the slope of the apertures at the front surface being in the range from about 10° or greater relative to a central axis extending through the apertures, preferably from about 10° to 20° relative to the central axis extending through the apertures, and more preferably being in the range from about 10° to 15° relative to the central axis.

Referring now to the figures, an exemplary embodiment of a nebulizing apparatus 10 will be described. As best illustrated in FIG. 3, the nebulizing apparatus 10 includes a disposable mouthpiece assembly 12 and a removable oscillating assembly 14. Referring to FIG. 1, construction of the mouthpiece assembly 12 will be described. The mouthpiece assembly 12 includes an elongate tubular housing 16 having a proximal end 18 and a distal end 20. At the distal end 20 is a mouthpiece 22, while a liquid supply cartridge 24 is at the proximal end 18. As will be described in grater detail hereinafter, a carrier plate 26 extends from the housing 16 and is provided to hold a thin shell member within the housing 16. An elastomeric O-ring 28 is placed adjacent the carrier plate 26 and is positioned against a vibrating beam as described in greater detail hereinafter. To dynamically isolate the carrier plate 26, the housing 12 is preferably constructed of an elastomeric material, preferably having a modulus of elasticity of about 100 psi to 150 psi.

Referring to FIG. 2, the interior of the mouthpiece assembly 12 will be described. The tubular housing 16 forms a central chamber 32 having an opening 34 at the mouthpiece 22. Annularly extending into the central chamber 32 is the carrier plate 26. In turn, the carrier plate 26 is attached about a thin shell member 36 having a front surface 38 and a rear surface 40. Extending between the front surface 38 and rear surface 40 are a plurality of tapered apertures (not shown) having the smaller opening at the front surface 38 and the larger opening at the rear surface 40. Upon vibration of the carrier plate 26, the thin shell member 36, is vibrated so that liquid may be ejected through the apertures and from the front surface 38 as described hereinafter.

An amount of liquid 42 is supplied to the rear surface 40 from the liquid supply cartridge 24. The liquid cartridge 24 includes a divider 44 that separates the liquid supply cartridge 24 into an air volume 46 and a liquid volume 48. To dispense liquid from the liquid volume 48, the liquid supply cartridge 24 is squeezed to force liquid in the liquid volume 48 through a nozzle 50 where it comes into contact with the rear surface 40 of the thin shell member 36. The cartridge 24 becomes permanently deformed when squeezed so that the liquid 42 delivered to the rear surface 40 will not be withdrawn back into the liquid volume 48. The size of the air volume 46 will be configured such that all of the liquid within the liquid volume 48 will be transferred from the liquid volume 48 when the cartridge 24 is squeezed.

The liquid 42 delivered from the supply cartridge 24 will usually be held to the rear surface 40 solely by surface tension forces. In this way, the liquid 42 may remain in contact with the rear surface 40 until ejected and without the need for a separate chamber to hold the liquid 42 against the rear surface 40. To eject the liquid 42 from the front surface 38, the carrier plate 26 is vibrated to in turn vibrate the thin shell member 36. The liquid 42 adhering to the rear surface then passes through the apertures and from the front surface 38 as described in U.S. Pat. No. 5,164,740 and copending application serial numbers 08/163,850 filed Dec. 7, 1993 and 08/417,311, filed Apr. 5, 1995, the entire disclosures of which are herein incorporated by reference.

The thin shell member 36 is preferably formed of a thin, rigid material having a hemispherical geometry. Alternatively, the thin shell member 36 may be parabolic, arc shaped, or curved in geometry. The thin shell member 36 will have a very high bending stiffness which will allow it to follow the vibratory motion of the carrier plate 26 as a rigid body. In this way, the entire thin shell member 36 will vibrate in unison so that all apertures are subject to the same amplitude of vibration. Such vibration will assist in ejecting uniformly sized droplets (i.e. having a respirable fraction (RF) of greater than about 70%, preferably more than about 80%, and most preferably more than about 90%) simultaneously from most or all of the apertures. The spray produced by the thin shell member 36 is dispensed into the central chamber 32 in the direction of the opening 34. In this manner, as the patient inhales from the mouthpiece 22, the spray within the central chamber 32 will be drawn into the patient's lungs.

Figure 8:
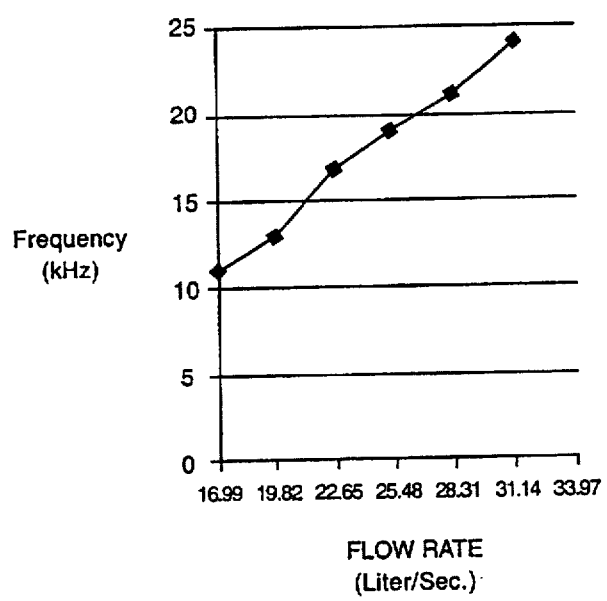

To control the time and/or rate at which the spray is produced, the mouthpiece assembly 12 further includes an acoustic chamber 52 having holes 54 and 56. Upon inhalation, air within the central chamber 32 passes through the holes 54 and 56 to produce an acoustic tone. This tone may be detected as described in greater detail hereinafter and used to determine both when the patient is inhaling and the patient's inspiratory flow rate. Such a signal may then be used to actuate the oscillating assembly which vibrates the thin shell member 36. Such a signal may be employed to control the time at which the shell member 36 is vibrated, e.g., such as only during inhalation. Alternatively, such a signal may also be employed to vibrate the thin shell member 36 at a frequency corresponding to the inspiratory flow rate. FIG. 8 illustrates one example of acoustical frequencies that may be produced for various inspiratory flow rates. For instance, an inspiratory flow rate of about 20 liters per second will generate an acoustical frequency of about 15 kHz. In turn, the detected frequency may be employed to drive the thin shell member 36.

Referring now to FIG. 3, operation of the combined mouthpiece assembly 12 and the oscillating assembly 14 will be described. The mouthpiece assembly 12 will preferably be constructed so that it may be removably attached to the oscillating assembly 14. In this manner, the mouthpiece assembly 12 may be discarded after use, while the oscillating assembly 14 which will not come into contact with the liquid may be reused. One particular advantage of such a configuration is that the mouthpiece assembly 12 may be constructed relatively inexpensively by not including an internal oscillator. Since the oscillating assembly 14 may be reused, costs to the patient are reduced.

Figures 4, 5:
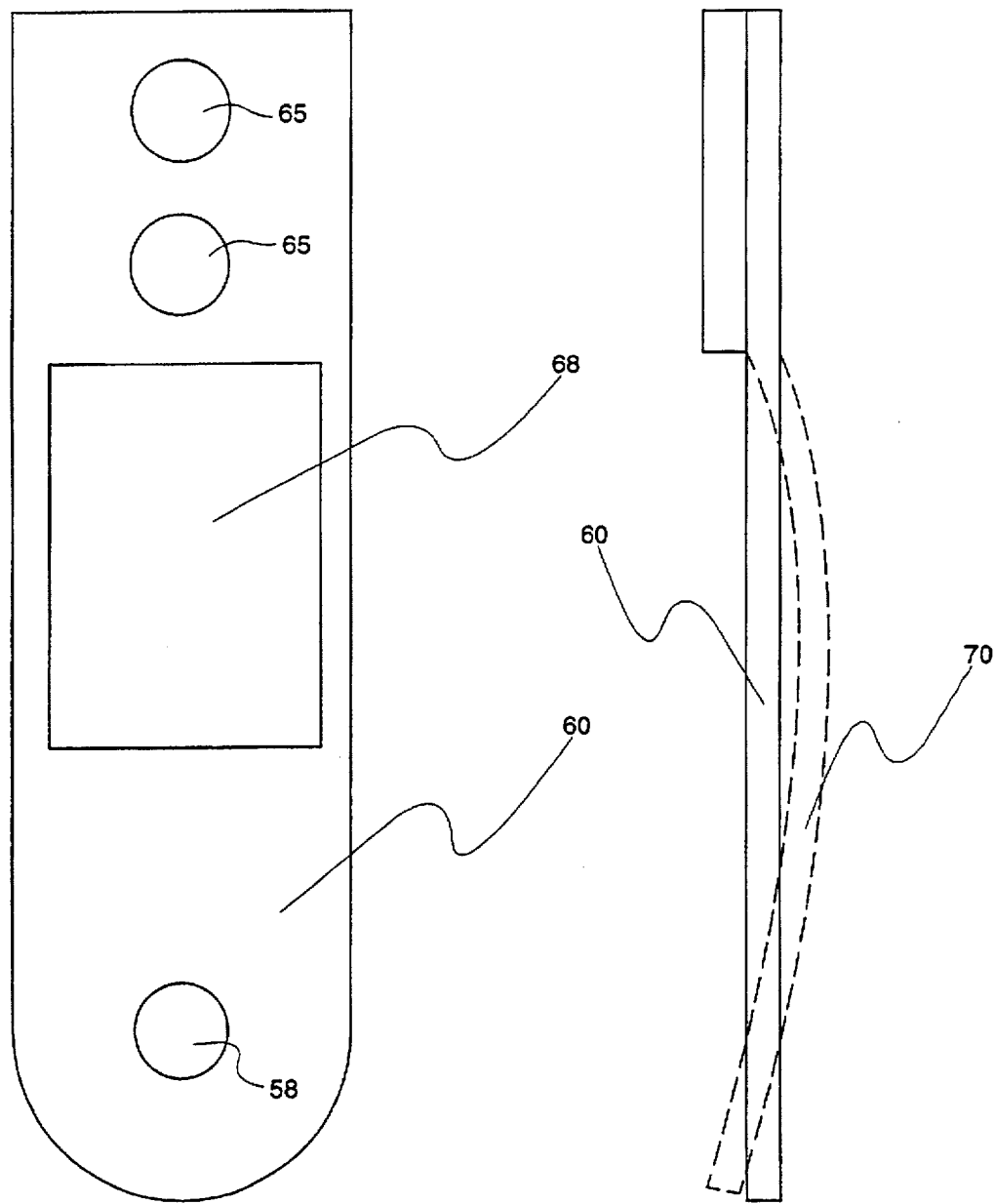

The mouthpiece assembly 12 is connected to the oscillating assembly 14 by sliding the proximal end 18 of the mouthpiece assembly 12 through an opening 58 (see FIG. 5) in a cantilever beam 60 of the oscillating assembly 14 until the o-ring 28 engages and is secured against the cantilever beam 60 as indicated by the arrows. A latching mechanism (not shown) may optionally be provided to removably latch the mouthpiece assembly 12 to the cantilever beam 60.

The cantilever beam 60 is provided with a free end 62 and a fixed end 64. The fixed end 64 is attached to an electronic circuit board 66 by a pair of screws 65, thus limiting the ability of the fixed end 64 to vibrate. On the other hand, the free end 62 which is attached to the mouthpiece assembly 12 is free to vibrate. A piezoelectric element 68 is bonded to the beam 60 and transmits vibratory motion to the beam 60. The dimensions of the beam 60 may be varied depending on the frequency of vibration. In one particular embodiment which is usually vibrated at 45 kHz to 200 kHz, the beam 60 will preferably have a length of about 30 mm to 80 mm, preferably at about 40 mm, a width of about 8 mm to 15 mm, preferably at about 12 mm, and a thickness of about 0.5 mm to 1 mm, preferably at about 0.7 mm. Such a beam will preferably be oscillated at a frequency of about 45 kHz which corresponds to the natural frequency of the beam. When vibrated, the beam 60 will have an oscillation mode shape 70 as illustrated in phantom line in FIG. 5.

Upon vibration of the cantilever beam 60, the elastomeric material of the housing 16 prevents transfer of vibratory energy through the tubular housing 16. In this manner, only the carrier plate 26 and the adjacent portion of the housing 16 are vibrated so that only minimal energy is needed to sufficiently vibrate the thin shell member 36. The cantilever beam 60 will preferably be vibrated to produce an oscillation amplitude of about 0.001 mm at the free end 62. Such vibration is transferred to the thin shell member 36 via the carrier plate 26 to produce a fine spray particles having a desired respirable fraction (RF).

In one experiment, the apparatus 10 of FIG. 3 was vibrated at a frequency of 45 kHz, and the particle size and distribution was measured by a particle sizer commercially available from Malvern Instruments Inc. (Southburrow, Mass.). The results indicated that about 94.99% of the particles were in the range from 1 to 6 micron with a flow rate of about 10 cubic µl per second.

To operate the nebulizing apparatus 10, the patient first attaches the mouthpiece assembly 12 to the oscillating assembly 14 as previously described. The liquid supply cartridge 24 is then squeezed to transfer the liquid to the rear surface 38 of the thin shell member 36. The patient then places his mouth over the mouthpiece 22 and begins to inhale. As air is drawn through the central chamber 32, an acoustic tone is produced by the acoustic chamber 52. As illustrated in FIG. 3, the acoustic tone may be detected by a microphone 72 on the circuit board 66. The detected acoustic signal is then processed by the circuit board 66 and is used to drive the piezoelectric element 68 at a frequency proportional to the acoustical frequency. In this manner, spray begins to eject from the thin shell member 36 upon inhalation, and at a rate that is proportional to the inspiratory flow rate. After the patient has fully inhaled, the acoustic signal ceases, thereby ceasing vibration of the piezoelectric element 68. If all of the liquid has not been dispensed, the patient may again inhale as previously described until all of the liquid has been delivered to the patient's lungs.

Figure 6:
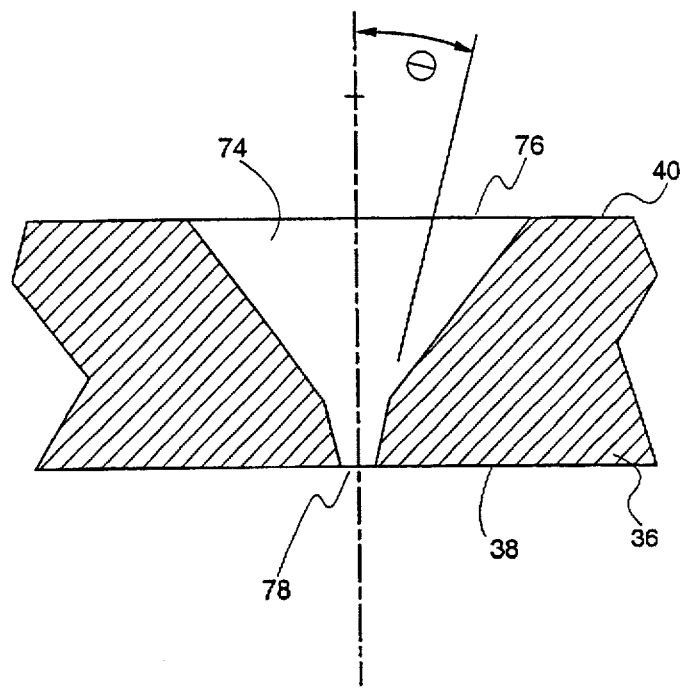

Referring to FIG. 6, an exemplary embodiment of an aperture 74 that may be included in the thin shell member 36 will be described. The aperture 74 has a conical shape, with a large opening 76 being at the rear surface 40 and a small opening 78 being at the front surface 38. At the small opening 78, the aperture 74 will have a slope, θ, measured relative to a central axis extending through the aperture 74. The slope θ at the small opening 78 will preferably be in the range from about 10° to 20°, more preferably in the range from about 10° to 15° and most preferably at about 15°. As the aperture 74 approaches the large opening 76, the slope may increase as illustrated. Preferably, the slope of the aperture 74 at the large opening 76 will be about 45° relative to the central axis, although the angle is not as critical as near the small opening. The slope of the aperture 74 near the small opening 78 is particularly important since ejection from the thin shell member 36 will occur at the front surface 36 where the small opening 78 is located. The slope, θ, should usually be at least about 10° with respect to the axis of the aperture to insure optimal ejection.

Figure 7:
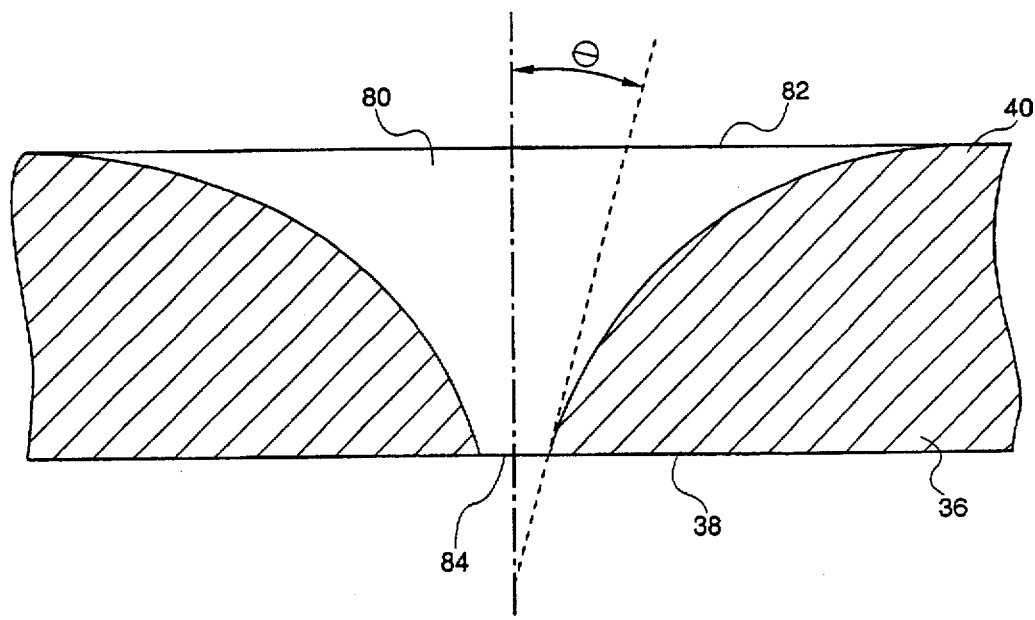

Referring to FIG. 7, an alternative aperture 80 for the thin shell member 36 will be described. The aperture 80 is conical and has a large opening 82 at the rear surface 40 and a small opening 84 at the front surface 38. When viewed in cross-section, the aperture 80 is formed of portions of two circles, with each circle having the same radius. The circles are positioned so that the slope θ at the small opening 84 will be in the range from about 10° to 20° relative to the central axis, more preferably from about 10° to 15°, and most preferably at about 12°. When the small opening 84 is sized at about 3 microns and has a taper of about 12°, the ejection rate from the small opening 84 is approximately 100 times greater than a quadrant-edge aperture having a 0° slope at the small opening as described in Jorissen, A. L., *Discharged Measurement at Low Reynolds Number*, ASME, February 1956, pp. 365–368, the disclosure of which is herein incorporated by reference.

Figure 9:
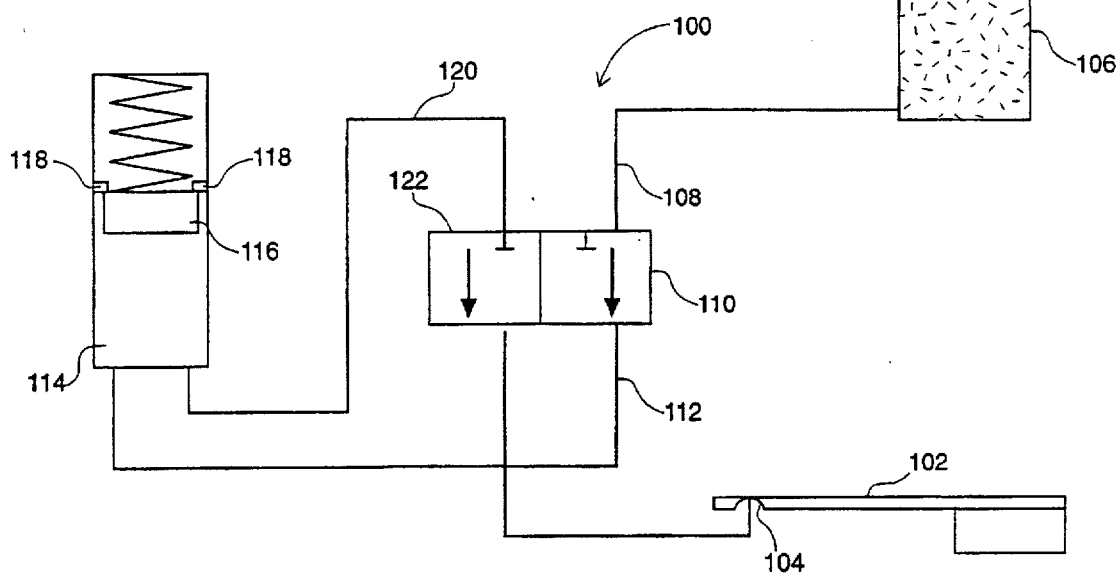
Figure 10:
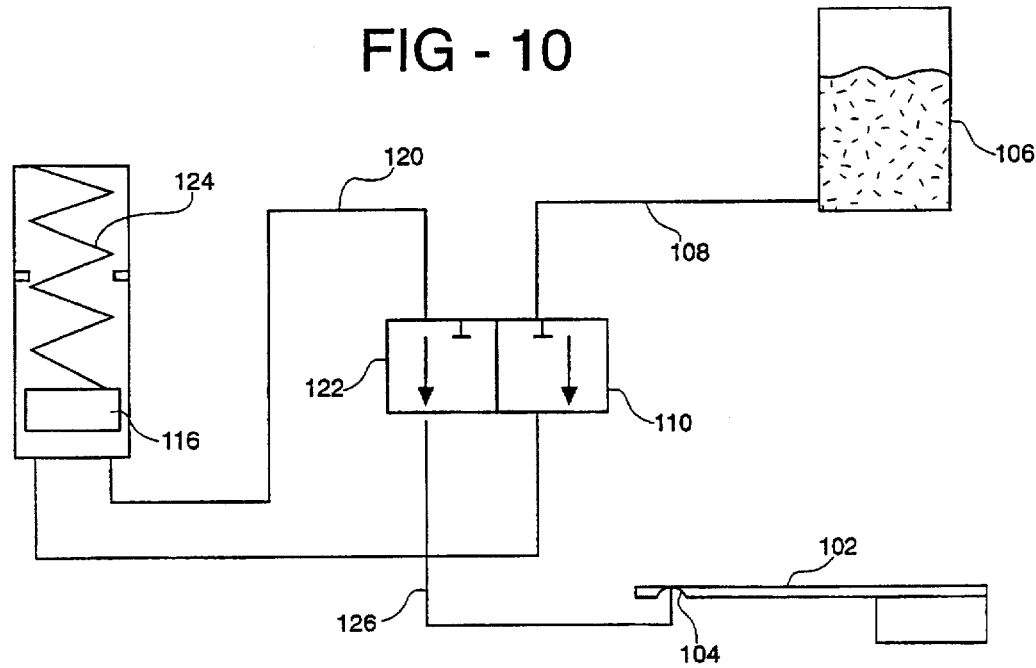

Referring to FIGS. 9 and 10, an exemplary system 100 for delivering a predetermined unit volume of liquid to a vibratable member 102 will be described. Vibratable member 102 vibrates a thin shell member 104 similar to the other thin shell members described herein so that liquid placed in surface tension with the rear side of the thin shell member 104 will be ejected from a front side. System 100 is provided so that only a predetermined unit volume of liquid will be supplied to the thin shell member 104. In this way, when vibratable member 102 is vibrated, the unit volume of liquid will be nebulized. Such a system is therefore advantageous in applications where a known volume of liquid is to be nebulized, such as when producing an aerosolized dosage of a medicament.

System 100 is provided with a source of liquid 106 which is preferably held under pressure. Liquid from source 106 passes through a line 108, through a valve 110 (shown in an open configuration), through a line 112, and into a metering chamber 114. Metering chamber 14 includes a spring biased piston 116 which is moved against a stop 118 when chamber 14 is filled with the liquid. When piston 116 is against stop 118, metering chamber 114 contains a unit volume so that when piston 116 is fully translated as shown in FIG. 10, a unit volume of liquid will be expelled into a line 120. Connected to line 120 is a valve 122 which is in a closed configuration in FIG. 9. In this way, the liquid within metering chamber 114 will be prevented from leaving until valve 122 is opened.

When metering chamber 114 is full, valve 110 is closed as shown in FIG. 10. Then, when a unit volume of liquid is ready to be supplied to thin shell member 104, valve 122 is opened. When valve 122 is opened, piston 116 translates by force of a spring 124 to force a unit volume of liquid out of metering chamber 114. In turn, a unit volume of liquid is delivered to thin shell member 104 through a line 126. The system lines will preferably be small enough so that minimal liquid will remain in the lines after being expelled from chamber 114, thereby allowing substantially all of the unit volume to de delivered to thin shell member 104. This unit volume is in the range from about 30 µl to about 70 µl, and more usually about 50 µl in volume and adheres to thin shell member 104 by surface tension. As vibratable member 102 is vibrated, the unit volume of liquid delivered to thin shell member 114 will be nebulized.

Figure 11:
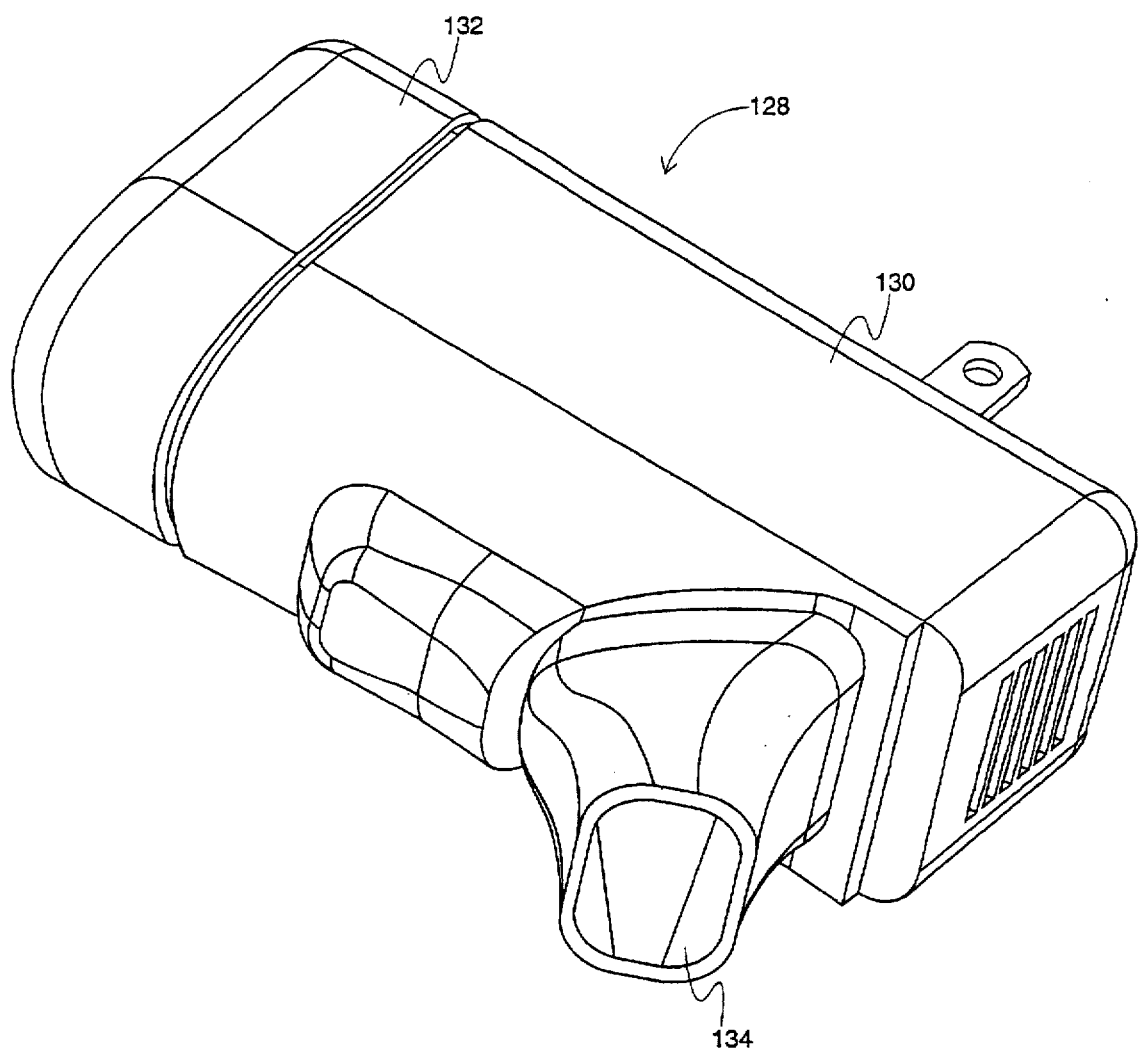

Referring now to FIG. 11, an exemplary embodiment of an apparatus 128 for nebulizing a unit volume of liquid will be described. Apparatus 128 includes a housing 130, a removable top end 132, and a mouthpiece 134. When top end 132 is depressed, a unit volume of a liquid is made available for nebulization as described in greater detail hereinafter.

Figure 12:
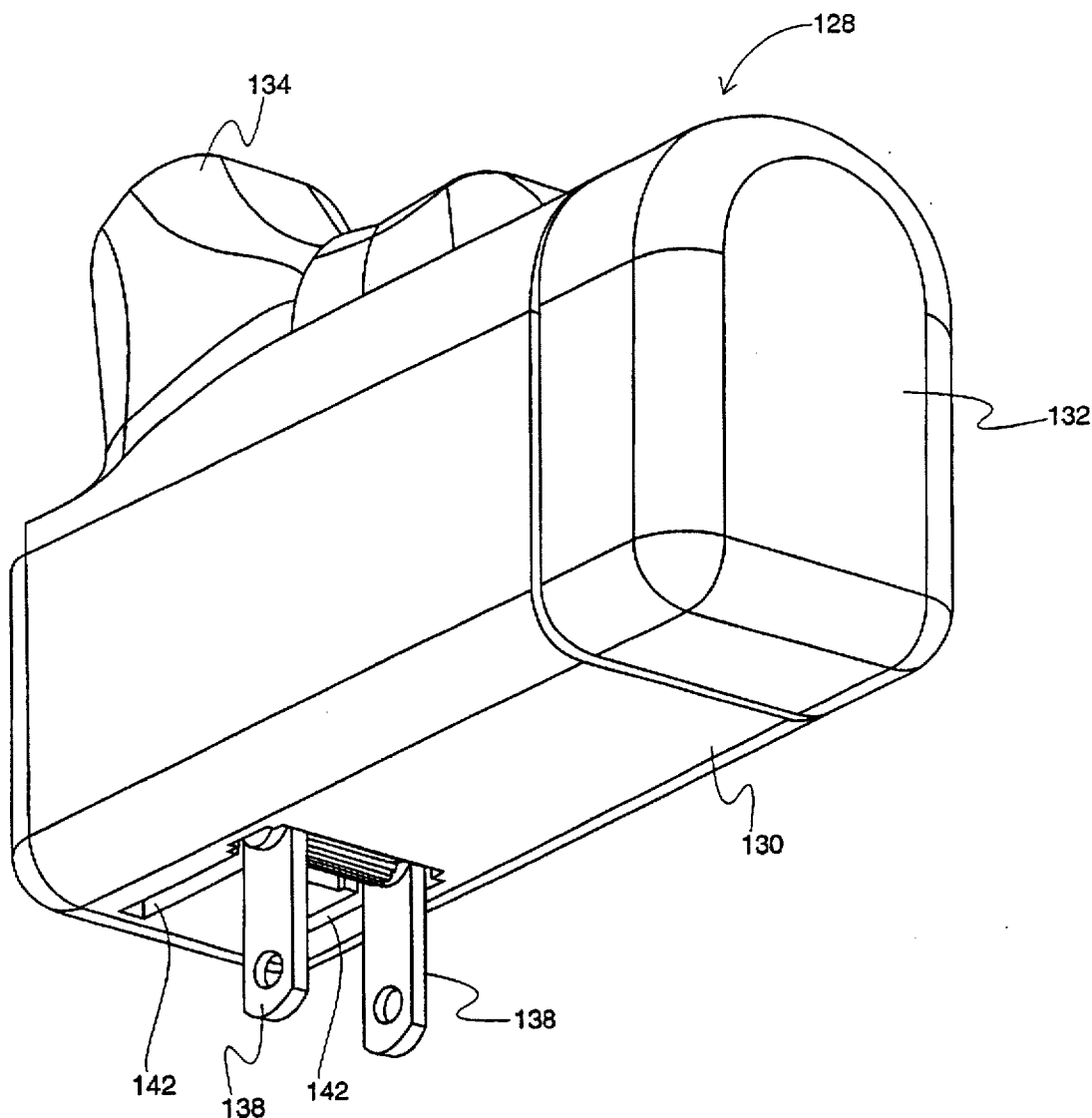

As best shown in FIG. 12 (which is a rear view of FIG. 11), apparatus 128 may optionally include a pair of flip blades 138 which may be inserted into an AC adapter or outlet to recharge batteries 140 (see FIG. 13) which supply power to apparatus 128. After recharging, flip blades 138 may be rotated and placed within slots 142 for convenient storage. Although shown with rechargeable batteries, apparatus 128 may have power supplied by any of a variety of power sources including DC power supplies, AC power supplies, batteries, including rechargeable batteries, and the like.

Figure 13:
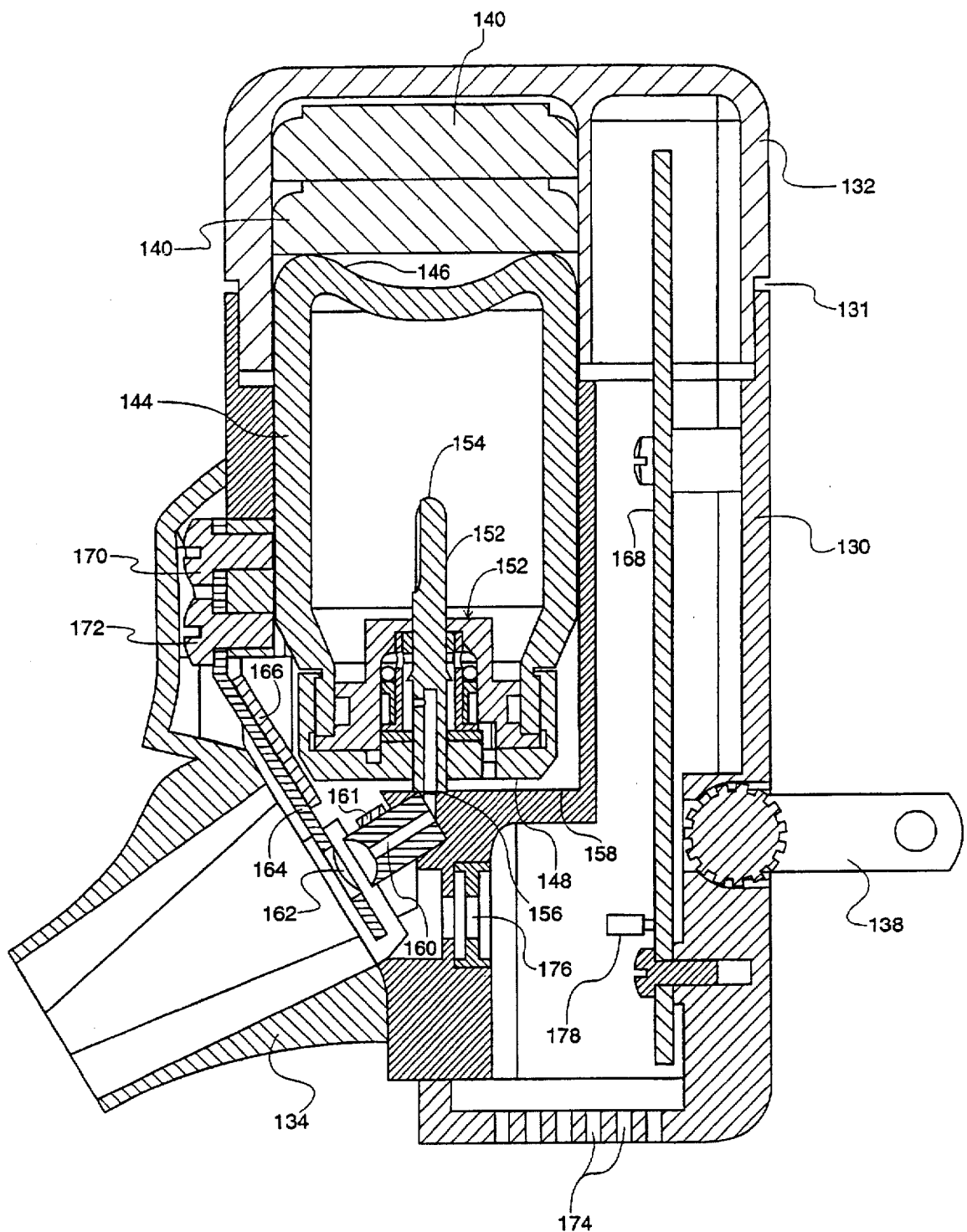

Referring to FIG. 13, construction of apparatus 128 will be described in greater detail. Apparatus 128 includes a container 144 having a top end 146 and bottom end 148. When within housing 130, top end 146 is positioned against batteries 140 so that a gap 131 is provided between top end 132 and housing 130 as shown. Bottom end 148 includes a valve 150 having a stem 152 with a proximal end 154 and a distal end 156. Distal end 156 rests on a shelf 158 so that when top end 132 is depressed, the gap 131 between top end 132 and housing 130 is closed. In turn, stem 152 is translated further into container 144 to deliver a unit volume of liquid into a passage 160 where it will be delivered to a rear surface of a thin shell member 162 of a vibratable member 164. Thin shell member 162 may be constructed similar to other embodiments described herein so that when vibratable member 164 is vibrated, liquid on the rear surface of thin shell member 162 will be dispensed from the front surface. Thin shell member 162 is shown in greater detail in FIG. 13A. In FIG. 13A, a side view of thin shell member 162 is shown with a plurality of tapered apertures 163 from which the liquid is ejected as previously described with other embodiments.

Vibratable member 164 is caused to vibrate by a piezoelectric element 166. Piezoelectric element 166 in turn is electrically connected to a printed circuit board 168 by wires (not shown), with the circuit board 168 having the electronics necessary to vibrate piezoelectric element 166. Vibratable member 164 may be constructed similar to and vibrated at frequencies similar to those previously described herein and in U.S. Pat. No. 5,164,740 and U.S. patent application Ser. Nos. 08/163,850, filed Dec. 7, 1993 and 08/417,311, filed Apr. 5, 1995, previously incorporated by reference. Power is supplied to circuit board 168 from batteries 140, which may optionally be rechargeable as previously described.

Vibratable member 164 is fixedly attached housing 130 by a pair of mounting screws 170 and 172. Vibratable member 164 is bent so that thin shell member 162 will be positioned to eject liquid into mouthpiece 134.

As a patient draws upon mouthpiece 134, air is drawn into housing 130 through a plurality of air inlets 174. In this manner, outside air sweeps through an acoustic chamber 176 so that the patient may inhale nebulized liquid produced from the thin shell member 162. Acoustic chamber 176 is used in combination with a microphone 178 on circuit board 168 to control actuation of piezoelectric element 166. Such an operation is similar to the embodiment of FIGS. 1 and 2 as previously described. Hence, when a patient inhales from mouthpiece 134, air drawn through acoustic chamber 176 will produce an acoustic sound, preferably outside the audible range, which is detected by microphone 178. In turn, circuit board 168 sends a signal to actuate piezoelectric element 166 to vibrate vibratable member 164. In this way, liquid is nebulized when the patient begins to inhale. When inhalation is stopped, microphone 178 will detect a stoppage of the acoustical signal so that vibration of vibratable member 164 will be stopped. The patient may continue to inhale from mouthpiece 134 until the entire unit volume of liquid at the rear surface of thin shell member 162 is dispensed. In this way, it may be assured that only a unit volume of liquid will be delivered to the patient (and on demand) since only a unit volume of liquid will be delivered to thin shell member 162. Further, little or no liquid will be wasted since the volume of liquid at the rear surface of thin shell member 162 will be nebulized only during inhalation from mouthpiece 134.

Apparatus 128 further includes an acoustical sensor 161 to detect when the unit volume of liquid has been ejected from thin shell member 162. Sensor 161 preferably comprises a piezoelectric element which vibrates from an acoustical signal generated when liquid adheres to the rear surface of thin shell member 162. When all of the liquid is ejected, sensor 161 will cease to vibrate indicating that all of the liquid has been nebulized.

Figure 14:
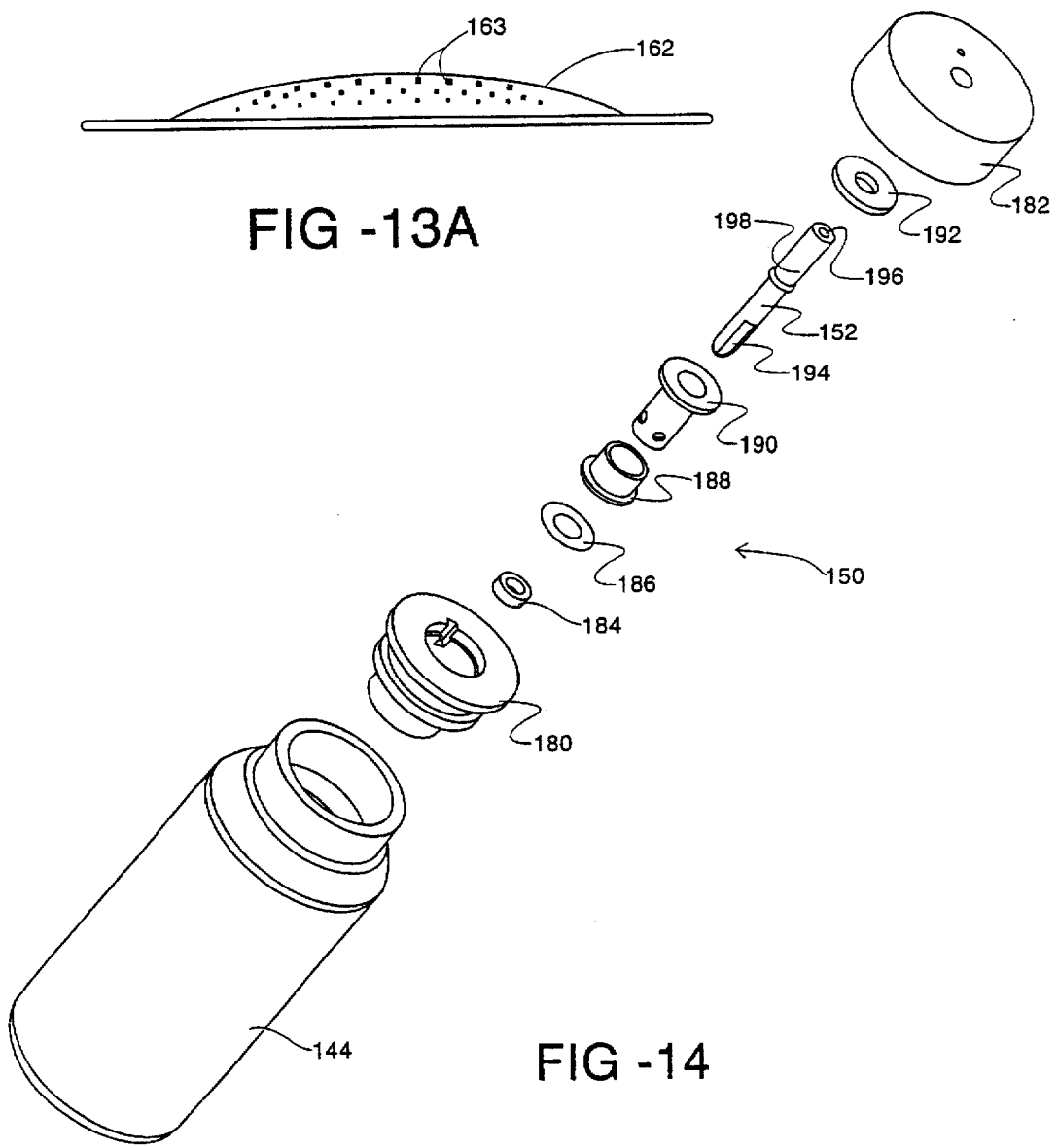
Figure 15:
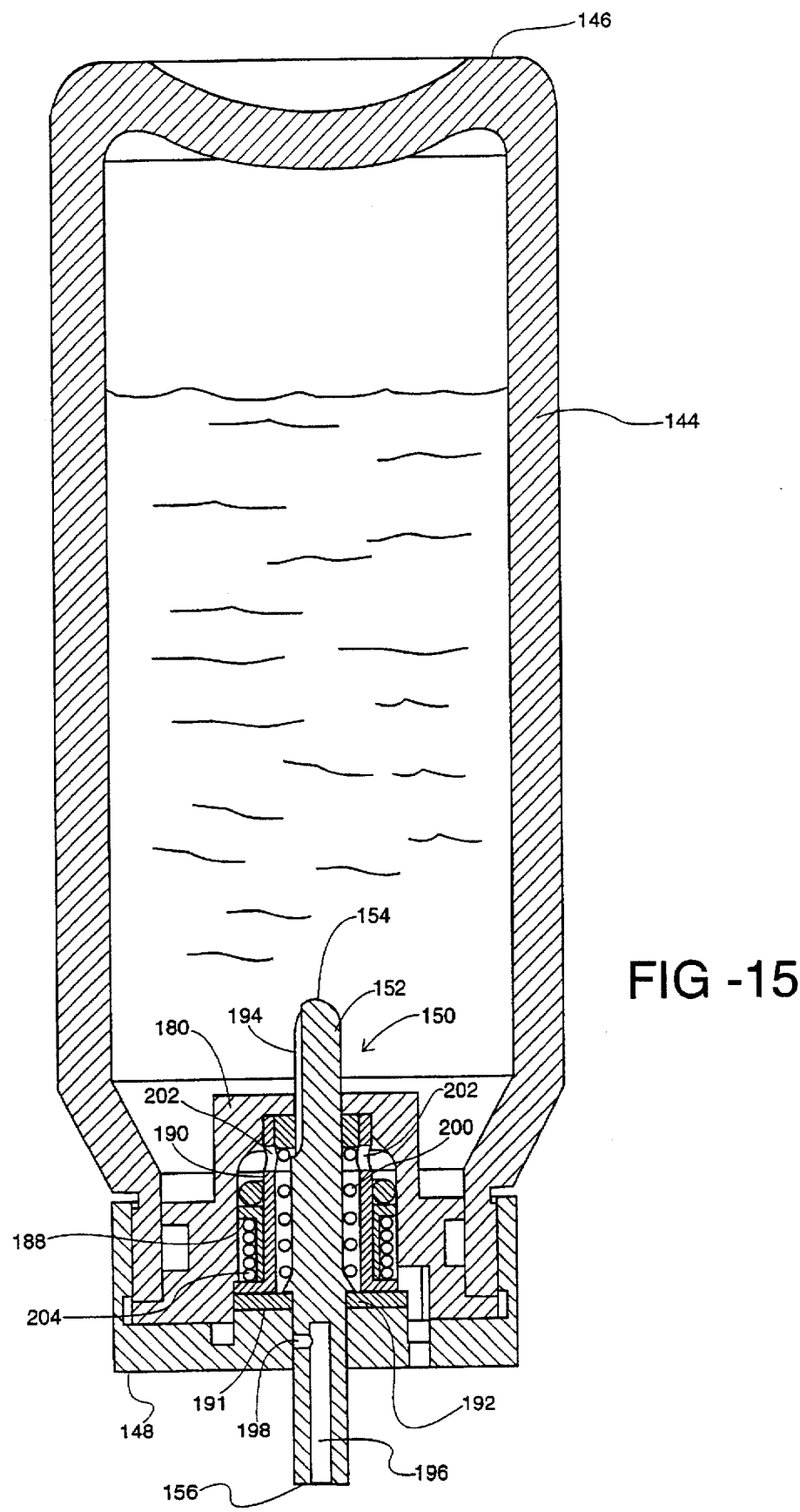
Figure 16:
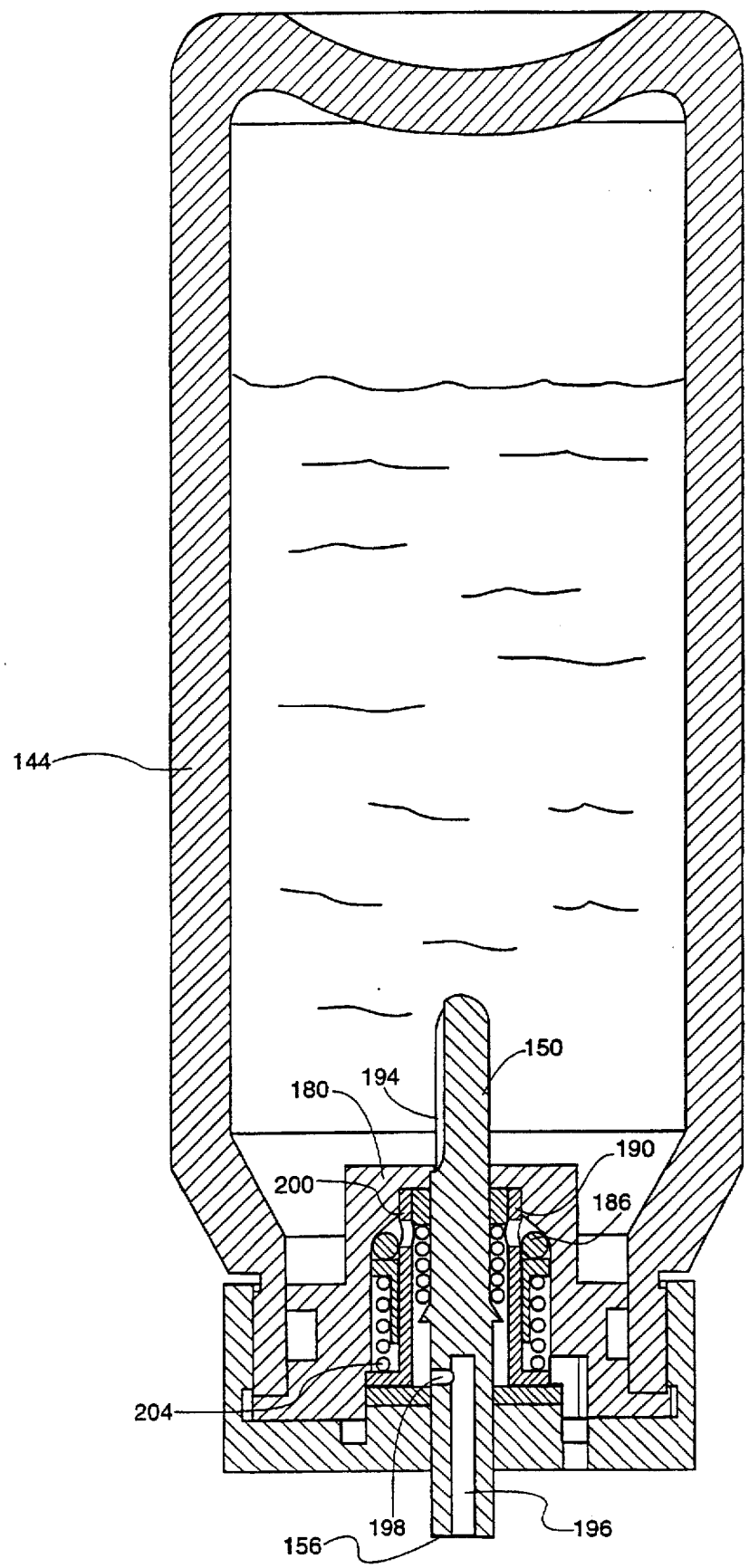

Referring now to FIGS. 14–16, construction of container 144 and valve 150 will be described. Container 144 is constructed of a rigid material, such as aluminum, so that container 144 may hold a volume of liquid under pressure.

Exemplary gases for holding liquid within container 144 under pressure include Nitrogen, air, or any inert gases, and the like. It will be understood that while the liquid within container 144 is held under pressure, container 144 will not include a propellant solution or an aerosol generating chemical as is typically used with conventional aerosol devices, such as MDI's. As such, container 144 will be positioned such that top end 146 is positioned vertically above bottom end 148 (see FIG. 15) so that the liquid will be in contact with valve 150.

As previously described, valve 150 includes stem 152 which is secured to container 144 by an insert 180 and a cap 182. Positioned over stem 152 is a cylindrical seal 184, an O-ring seal 186, a piston 188, a metering chamber member 190, and a washer 192. Stem 152 further includes an elongate groove 194 at proximal end 154. A lumen 196 extends through stem 152 at distal end 156 and terminates in a side port 198.

Valve 150 is shown in a closed configuration in FIG. 15. In the closed configuration, a first spring 200 biases a lip 191 of valve stem 152 against washer 192, thereby placing the interior of container 144 in fluid communication with the interior of metering chamber member 190 via groove 194. When in the closed configuration, the fluid within container 144 fills metering chamber member 190 and overflows into the space between insert 180 and metering chamber member 190 via holes 202. The pressurized liquid in turn translates piston 188 and compresses a second spring 204. Valve 150 is normally in the closed configuration so that as long as fluid remains within container 144, liquid will compress second spring 204 to fill valve 150 with liquid.

Dispensing of a unit volume amount of liquid from valve 150 is illustrated in FIG. 16. In FIG. 16, valve 152 is translated into container 144 until elongate groove 194 no longer provides a fluid path from container 144 into metering chamber member 190. At the same time, lumen 196 is placed in fluid communication with the interior of metering chamber member 190 via side port 198. At this point, second spring 204 expands (since the pressure in container 144 will not be available to keep it compressed) to axially translate both piston 188 and O-ring 186 within the space between insert 180 and metering chamber member 190. This in turn forces a unit volume of liquid from valve 150 where it will flow through lumen 196. After leaving lumen 196, the unit volume of liquid will flow to thin shell member 162 via passage 160 as previously described in connection in FIG. 13.

After the unit volume of liquid has been dispensed from valve 150, first spring 200 will again translate stem 152 against washer 192 as shown in FIG. 15 so that valve 150 may refill as previously described. In this manner, each time stem 150 is translated into container 144, a unit volume of liquid will be dispensed. Moreover, since substantially all of the liquid delivered to the thin shell member 162 will be nebulized, apparatus 128 may be employed to precisely deliver a unit dosage of a medicament to a patient.

Figure 17:
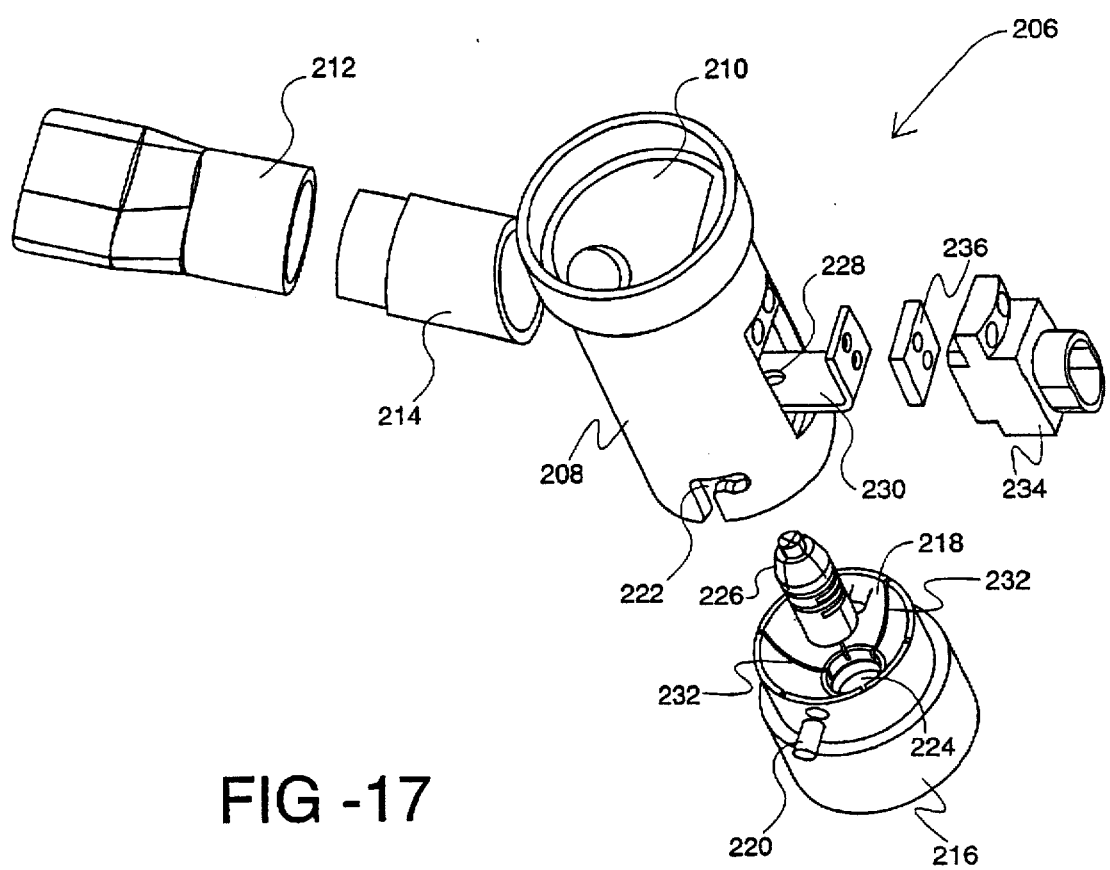
Figure 18:
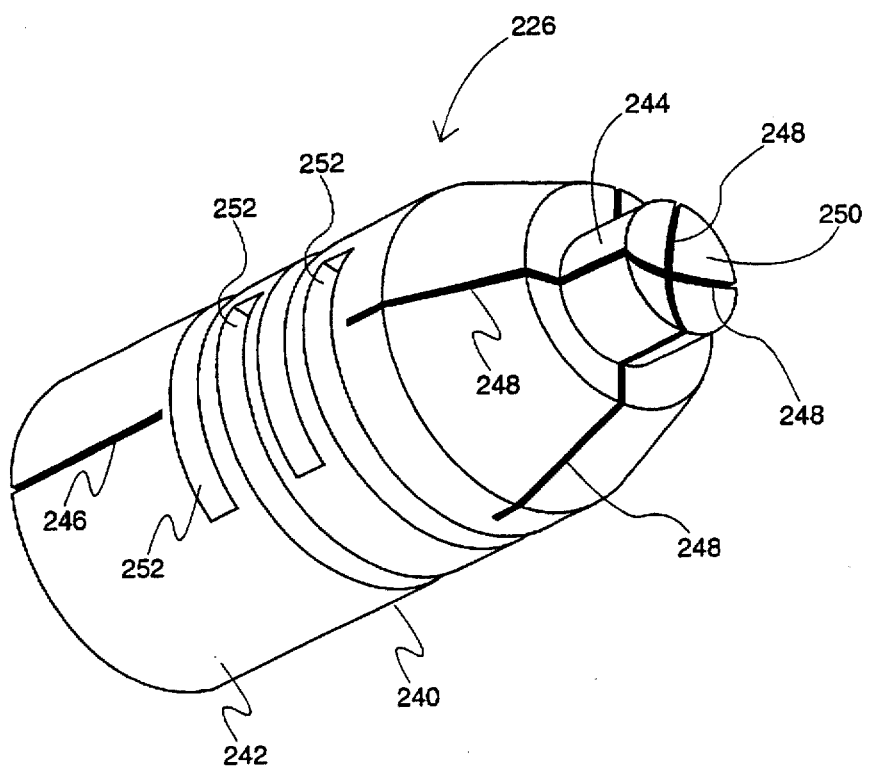
Figure 19:
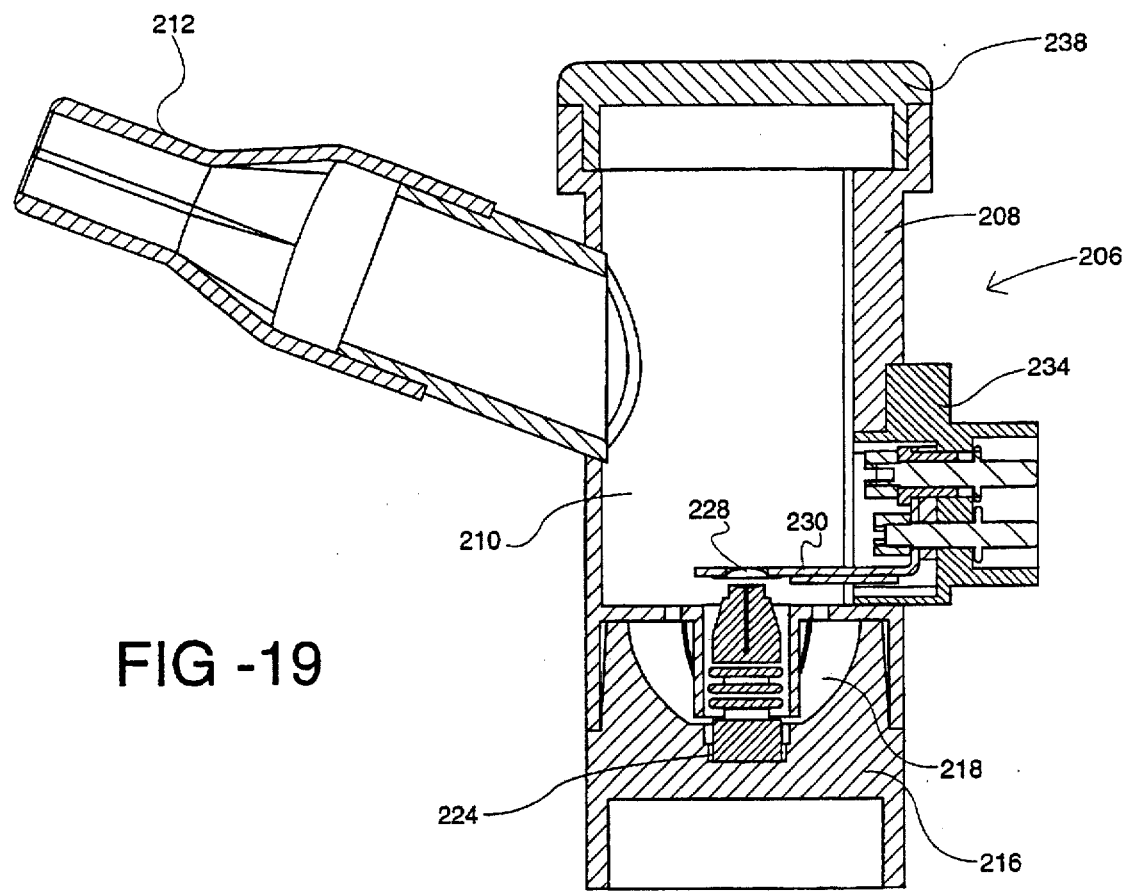
Figure 20:
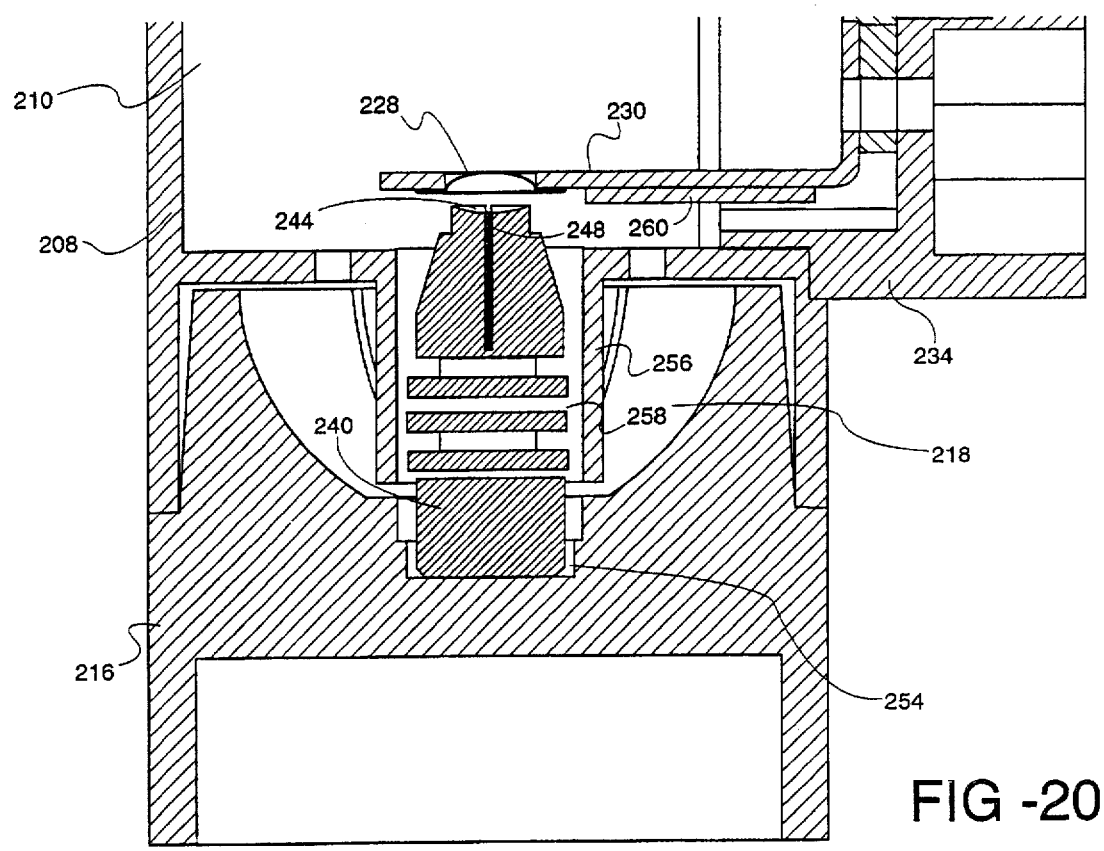
Figure 21:
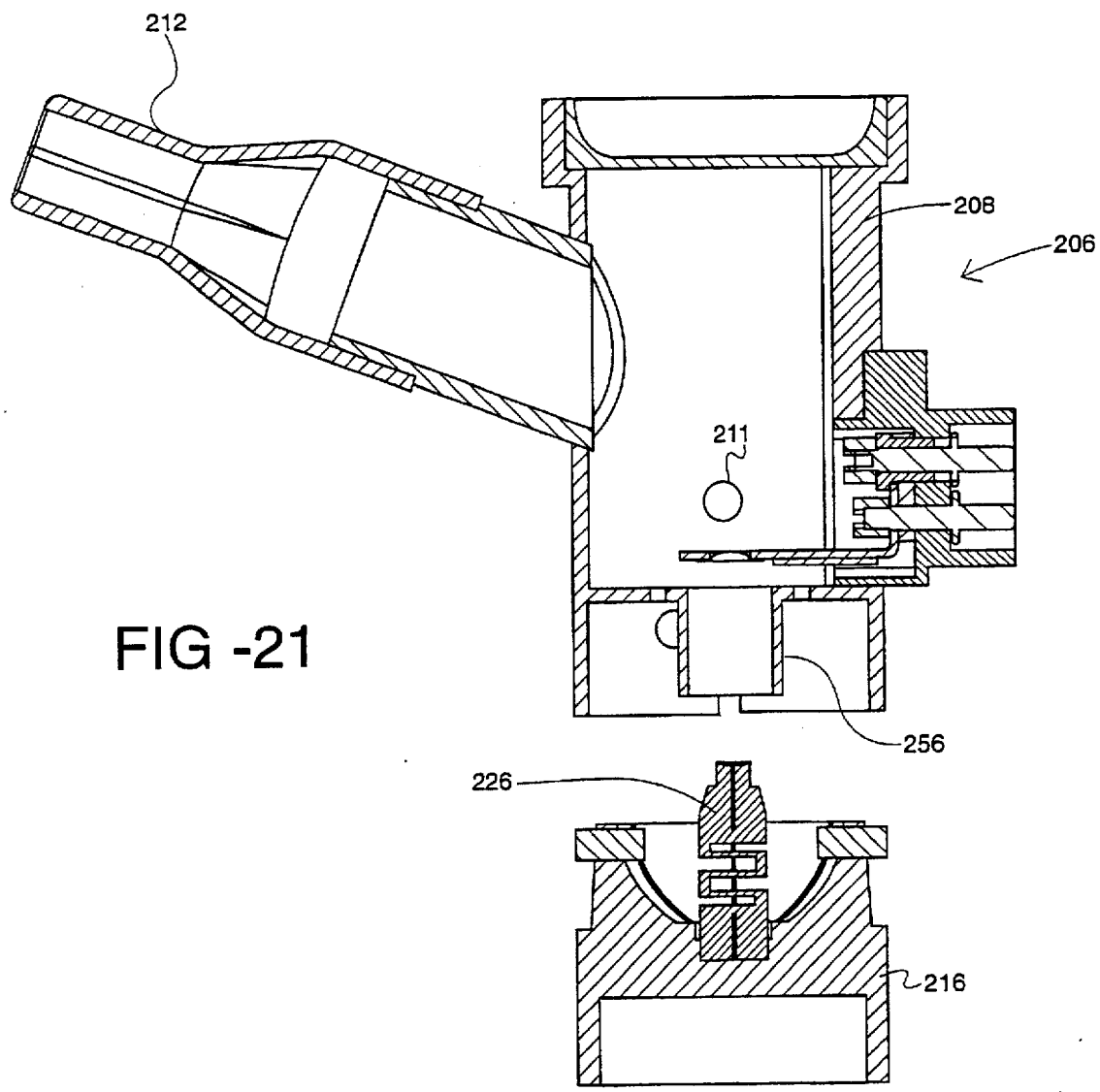
Figure 22:
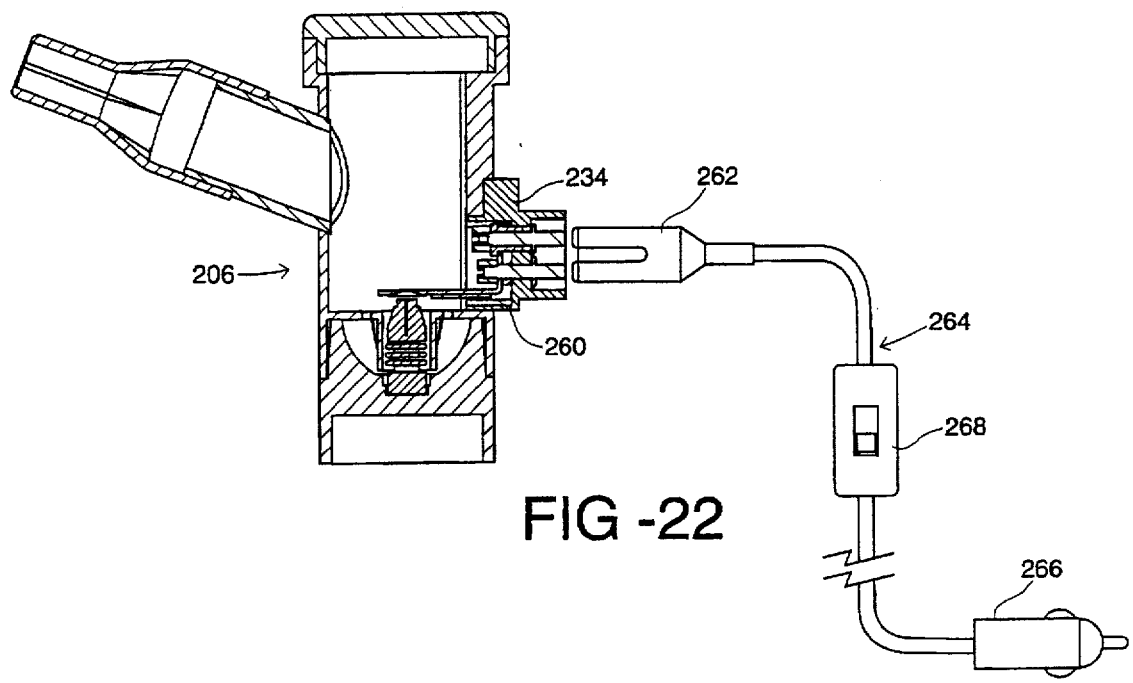
Figure 23:
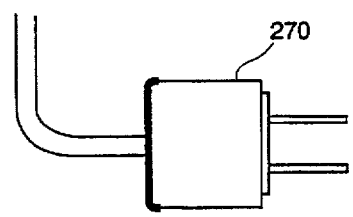

Referring now to FIG. 17, another exemplary embodiment of an apparatus 206 for nebulizing a liquid for prolonged treatments will be described. Apparatus 206 comprises a housing 208 which defines a chamber 210. A mouthpiece 212 is attached to housing 208 via a tube 214. Apparatus 206 further comprises a base 216 which defines a liquid reservoir 218. Base 216 includes a pin 220 which is placed within an L-shaped slot 222 on housing 208. In this manner, base 216 may be removably attached to housing 208 by inserting pin 220 into slot 222 and rotating base 216 clockwise relative to housing 208. Base 216 further includes a cylindrical opening 224 into which a wicking member 226 is received. As described in greater detail hereinafter, wicking member 226 draws fluid by capillary action from liquid reservoir 218 and to a thin shell member 228 of a vibratable member 230. To assist in drawing liquid at any orientation from liquid reservoir 218 into wicking member 226, liquid reservoir 218 may optionally include a plurality of capillary channels 232. Liquid reservoir 218 is provided with a generally concave geometry so that liquid held therein will tend to flow toward cylindrical opening 224 even when base 216 is significantly tilted. Capillary channels 232 further assist in drawing any liquid to cylindrical opening 224 by capillary action. In this manner, reservoir 218 is designed so that substantially all of the liquid placed therein will be distributed to cylindrical opening 224 where it may be drawn by wicking member 226 up to thin shell member 228. In this way, no significant amount of liquid will remain within reservoir 218, but will substantially all be nebulized.

Vibratable member 230 is connected to housing 208 via an adapter 234, which also functions as a connector for an external power supply. A mounting plate 236 is placed between adapter 234 and vibratable member 230. Vibratable member 230 and thin shell member 228 may be constructed essentially identical to embodiments previously described herein and will operate in a similar manner. A lid 238 (see FIG. 20) is provided to enclose chamber 210.

Referring to FIG. 18, construction of wicking member 226 will be described in greater detail. Wicking member 226 comprises an elongate body 240 having a cylindrical base portion 242 and a cylindrical tip 244. Base portion 242 may optionally include a capillary channel 246 to assist in drawing the liquid up the base portion 242. Additional capillary channels 248 are included in body 240 and extend up to tip 244 to assist in drawing up liquid to tip 244. Tip 244 further includes a concave well 250 which holds liquid drawn through capillary channels 248 so that the liquid may be nebulized by the thin shell member 228.

Although the size of capillary channels 248 may vary depending upon the type of liquid to be nebulized, capillary channels 248 will preferably have a gap in the range from about 50 μm to about 250 μm, and more preferably from about 100 μm to about 200 μm.

Preferably, tip 244 will be in contact with thin shell member 228 during vibration to ensure that liquid at tip 244 will be delivered to thin shell member 228. To ensure that wicking member 226 will not interfere with the vibration of thin shell member 228, wicking member 226 includes a plurality of cutouts 252 which provide body 240 with axial flexibility. The cutouts 252 therefore allow for manufacturing tolerances to be eased when constructing the wicking member. Body 240 will preferably be constructed of an ABS plastic (which has good wetting capabilities) so that, with the assistance of cutouts 252, body 240 will axially flex as thin shell member 228 is vibrated. Wicking member 226 may optionally be spring-loaded to prevent vibrational interference with vibratable member 230.

Referring now to FIG. 19, operation of apparatus 206 will be described. Initially, reservoir 218 is filled with an amount of liquid, such as a unit dosage of a liquid medicament. To assist in filling reservoir 218, base 216 may be separated from housing 208 as illustrated in FIG. 21. When filled, liquid within reservoir 218 will tend to settle (or be drawn into) opening 224. As best shown in FIG. 20, cylindrical opening 224 will be slightly spaced apart from cylindrical base portion 242 to provide an annular capillary gap 254 therebetween. Gap 254 will preferably be in the range from about 50 μm to about 250 μm, and more preferably from about 100 μm to about 200 μm. In this manner, liquid within opening 224 will be drawn vertically up wicking member 226 through capillary gap 254. Housing 208 further includes a cylindrical portion 256 which surrounds body 240 as shown. Cylindrical portion 256 provides an annular gap 258 which is similar in size to capillary gap 254. In this manner, liquid rising through capillary gap 254 will continue its travel up elongate body 240 via capillary cap 258. As the rising liquid reaches capillary channels 248, the liquid continues its travel toward tip 244 through capillary channels 248.

Vibratable member 230 includes a piezoelectric element 260 which vibrates thin shell member 228 as previously described to eject liquid into chamber 210. Hence, by employing wicking member 226, substantially all of the liquid supplied to reservoir 218 will be drawn to tip 244 where it may be nebulized by thin shell member 228. In this manner, it can be assured that all the liquid will be nebulized.

Referring back to FIG. 19, as thin shell member 228 nebulizes the liquid, a patient may inhale from mouthpiece 212 to drawn the nebulized liquid from chamber 210. Chamber 210 includes at least one air hole 211 so that air may be drawn through the mouthpiece 212 during patient inhalation.

As best shown in FIG. 21, upon completion of nebulization, base 216 may be removed from housing 208. In this manner, apparatus 206 may easily be cleaned. For example, once base 216 has been separated from housing 208, both pieces may be placed in a conventional dishwasher for cleaning and sterilization.

Referring now to FIG. 22, the manner of supplying power to apparatus 206 will be described. Adapter 234 is configured to receive a connector 262 of a DC adapter system 264. Adapter system 264 includes a male plug 266 which may by inserted into, for example, a twelve volt DC power source of an automobile. A switch 268 is provided to regulate delivery of power to apparatus 206. Switch 268 further includes a printed circuit board (not shown) which is similar to that board of FIG. 13 and which drives piezoelectric element 260 as previously described.

Alternatively, a variety of other power sources may be employed to operate apparatus 206. For example, as illustrated in FIG. 23, a conventional AC plug 270 may be provided to supply alternating current to apparatus 206. The alternating current will preferably be converted to DC power in order to drive piezoelectric element 206. Alternatively, internal batteries may be supplied to operate apparatus 206 similar to the embodiment of FIG. 11 as previously described.

Although the foregoing invention has been described in detail for purposes of clarity of understanding, it will be appreciated that certain changes and modifications may be practiced within the scope of the appended claims.

What is claimed is:

1. An apparatus for nebulizing a liquid, the apparatus comprising:

a non-planar member comprising a front surface, a rear surface, and a plurality of apertures extending therebetween, said apertures being tapered to narrow from the rear surface to the front surface;

a liquid supplier which delivers a predetermined unit volume of liquid to the rear surface; and a vibrator which vibrates the non-planar member to eject liquid droplets from the front surface of the non-planar member.

2. An apparatus as in claim 1, wherein the tapers have a size in the range from about 1 μm to 6 μm at their narrowest dimension.

3. An apparatus as in claim 1, wherein the liquid comprises a medicament.

4. An apparatus for nebulizing a liquid, the apparatus comprising:

a non-planar member comprising a front surface, a rear surface, and a plurality of apertures extending therebetween, said apertures being tapered to narrow from the rear surface to the front surface;

a liquid reservoir; and a capillary system in fluid communication with the liquid reservoir, said capillary system being disposed to draw liquid from the reservoir by capillary action for delivery to the rear surface of the non-planar member; and a vibrator which vibrates the non-planar member to eject liquid droplets from the front surface of the non-planar member.

5. An apparatus as in claim 4, wherein the capillary system comprises a wicking member having a bottom end within the liquid reservoir and a delivery end near the rear surface of the non-planar member and an outer member spaced-apart from the wicking member by a capillary gap so that liquid from the reservoir may be drawn toward the delivery end by capillary action.

6. An apparatus as in claim 5, wherein the wicking member further includes at least one capillary channel at the delivery end so that liquid delivered from the capillary gap may continue its travel to the rear surface of the non-planar member through the capillary channel.

7. An apparatus as in claim 5, wherein a bottom portion of the wicking member is cylindrical in geometry and wherein the outer member includes an annular body which surrounds the wicking member.

8. An apparatus as in claim 5, further comprising a housing having a chamber and a mouthpiece, and wherein the outer member is attached to the housing.

9. An apparatus as in claim 8, wherein the wicking member is attached to the liquid reservoir, and wherein the liquid reservoir is detachably secured to the housing so that the liquid reservoir may be separated from the housing.

10. An apparatus as in claim 5, wherein the wicking member includes a flexible portion so that it may axially flex upon contact with the vibrating member.

11. An apparatus as in claim 5, wherein the liquid reservoir has a concave shape and includes capillary channels which move the liquid toward the capillary gap between the outer member and the wicking member.

12. An apparatus as in claim 4, further comprising a power supply which supplies power to the vibrator.

13. An apparatus as in claim 12, wherein the power supply comprises a rechargeable battery.

14. A method for nebulizing a liquid, the method comprising:

providing a non-planar member comprising a front surface, a rear surface, and plurality of apertures extending therebetween, said apertures being tapered to narrow from the rear surface to the front surface;

drawing liquid from a liquid reservoir by capillary action to place the liquid in contact with the rear surface of the non-planar member; and vibrating the non-plannar member to eject the liquid on the rear suface from the front surface, wherein liquid is continuously supplied from the liquid reservoir to the rear surface as the non-planar member is vibrated.

15. A method as in claim 14, further comprising vibrating the non-planner member until substantially all of the liquid wihtin the resorvoir is depleted.

16. A method as in claim 15, wherein the liquid reservoir holds an amount of liquid equal to a unit dosage amount.

17. A method as in claim 14, wherein the capillary action is provided by a capillary gap between a wicking member and an outer member, with the wicking member having a bottom end within the liquid reservoir and a delivery end near the rear surface of the non-plannar member.

18. A method as in claim 17, wherein the capillary action is further provided by at least one capillary channel at the delivery end of the wicking member, wherein liquid from the capillary gap may continue its travel through the capillary channel.

19. A method as in claim 17, further comprising providing a housing having a chamber, a mouthpiece, the outer member, and the vibratable member, and further comprising attaching the reservoir to the housing prior to vibrating the vibratable member.

20. A method as in claim 19, further comprising detaching the housing from the reservoir and washing the housing and reservoir.

21. A method as in claim 19, further comprising tilting the housing while nebulizing the liquid, wherein a patient may inhale from the mouthpiece while lying down.

22. A method as in claim 17, further comprising transferring liquid from the liquid reservoir and to the capillary gap by capillary action.

* * * * *